(12) United States Patent
Spichal et al.

(10) Patent No.: US 8,222,260 B2
(45) Date of Patent: Jul. 17, 2012

(54) SUBSTITUTED 6-ANILINOPURINE DERIVATIVES AS INHIBITORS OF CYTOKININ OXIDASE/DEHYDROGENASE AND PREPARATIONS CONTAINING THESE DERIVATIVES

(75) Inventors: Lukas Spichal, Olomouc (CZ); Marketa Gemrotova, Petrovice u Karvine (CZ); Marek Zatloukal, Sumperk (CZ); Jitka Frebortova, Olomouc (CZ); Petr Galuszka, Olomouc (CZ); Tomas Werner, Berlin (DE); Thomas Schmulling, Berlin (DE); Karel Dolezal, Olomouc (CZ); Miroslav Strnad, Olomouc (CZ)

(73) Assignees: Univerzita Palackego V Olomouci, Olomouc (CZ); Freie Universitat Berlin, Berlin (DE)

( * ) Notice: Subject to any disclaimer, the term of this patent is extended or adjusted under 35 U.S.C. 154(b) by 161 days.

(21) Appl. No.: 12/666,189

(22) PCT Filed: Jul. 2, 2008

(86) PCT No.: PCT/CZ2008/000074
§ 371 (c)(1),
(2), (4) Date: Mar. 10, 2010

(87) PCT Pub. No.: WO2009/003428
PCT Pub. Date: Jan. 8, 2009

(65) Prior Publication Data
US 2010/0190806 A1    Jul. 29, 2010

(30) Foreign Application Priority Data
Jul. 4, 2007 (CZ) .............................. PV 2007-453

(51) Int. Cl.
A61K 31/52 (2006.01)
C07D 473/00 (2006.01)
(52) U.S. Cl. ..................................... 514/263.1; 544/264
(58) Field of Classification Search .................. 544/264; 514/263.1
See application file for complete search history.

(56) References Cited

U.S. PATENT DOCUMENTS
7,091,346 B1 * 8/2006 Zimmermann et al. ...... 544/277

OTHER PUBLICATIONS

Pedersen et al. CAS: 104:186245, 1986.*
Qu et al. CAS: 146: 401726, 2006.*
Bordon-Pallier et al. CAS: 137:78809, 2002.*
Qu et al. CAS: 145: 167482, 2006.*
Brill et al. CAS: 135: 257077, 2001.*
Fiorini et al. CAS: 128:230182, 1998.*
Erba et al. CAS: 128: 13236, 1997.*
Zimmermann et al. CAS: 127:34237, 1997.*
Yakout et al. CAS: 110:172972, 1989.*

* cited by examiner

*Primary Examiner* — Rei-tsang Shiao
(74) *Attorney, Agent, or Firm* — Notaro, Michalos & Zaccaria P.C.

(57) ABSTRACT

The invention relates to substituted 6-anilinopurine derivatives of the general formula I, wherein R denotes one to five substituents independently selected from the group consisting of hydrogen, halogen, hydroxyl, amino, alkyloxy and alkyl group, and R2 denotes amino, halogen, nitro, thio, alkylthio or alkyl group for use as inhibitors of cytokinin oxidase/dehydrogenase. The invention also relates to the compositions containing these derivatives.

9 Claims, 8 Drawing Sheets

SUBSTITUTED 6-ANILINOPURINE DERIVATIVES AS INHIBITORS OF CYTOKININ OXIDASE/DEHYDROGENASE AND PREPARATIONS CONTAINING THESE DERIVATIVES

TECHNICAL FIELD

The invention relates to substituted 6-anilinopurine derivatives, their use as inhibitors of cytokinin oxidase/dehydrogenase and preparations containing these derivatives.

BACKGROUND ART

In recent years, 6-substituted aminopurines have assumed considerable biochemical significance. Some compounds of this type promote plant growth and belong to the group of growth regulators termed cytokinins (Letham, Ann. Rev. Plant. Physiol. 18, 349, 1967). Kinetin ($N^6$-furfuryladenine) was the first molecule to be discovered with cytokinin activity. It was originally isolated from autoclaved herring sperm DNA (Miller et al. 1955, J. Am. Chem. Soc. 77:1392). Cytokinins closely related to kinetin occur also as modified bases in soluble RNA (Skoog et al., Science 154:1354, 1966). In the serine and tyrosine tRNAs of yeast, plants and animals the cytokinin is adjacent to the anticodon. The growth of mammalian cell cultures is inhibited by certain $N^6$-substituted adenosines with cytokinin activity (Grace et al., Proc. Am. Assoc. Cancer Res. 8:23, 1967).

Cytokinins are important plant hormones regulating many aspects of plant development. Recent studies on transgenic plants with altered cytokinin metabolism or signalling revealed interesting consequences of cytokinin deficiency or disruption of cytokinin perception (Werner et al, Proc. Natl. Acad. Sci. USA 98:10487, 2001, Werner et al, Plant Cell 15:2532, 2003; Riefler et al., Plant Cell 18:40, 2006). Modulation of cytokinin levels by exogenous application or regulation of their endogenous levels genetically through cytokinin oxidase/dehydrogenase (CKX, EC 1.5.99.12), a key enzyme involved in cytokinin degradation, have already shown possible applications in agriculture. For example, exogenous application of cytokinins led to shortening of the time to anthesis in tomato (Sawhney and Shukla, Am J Bot 81:1640, 1994) or reversion of male sterility in barley (Ahokas, Proc. Natl. Acad. Sci. USA 79:7605, 1992). Anther- and pollen-specific expression of CKX in maize was shown to be a potential tool for generating male sterility for production of hybrid varieties of traditionally non-hybrid crops (Huang et al., 2003). Recent work reported CKX involvement in regulation of rice grain production (Ashikari et al., Science 309: 741, 2005).

We have recently discovered that novel generations of CKX inhibitors could be based on 2-substituted 6-anilinopurines. The most promising substituents are 2-chloro, 2-fluoro and 2-amino groups in direction to specific CKX inhibitors preparation.

It is an object of this invention to provide cytokinin analogues having improved selectivity and efficiency index in the inhibition of cytokinin oxidase/dehydrogenase, i.e. that are less toxic yet more efficacious than the analogues known heretofore.

DISCLOSURE OF THE INVENTION

The object of this invention are substituted 6-anilinopurine derivatives of the general formula I

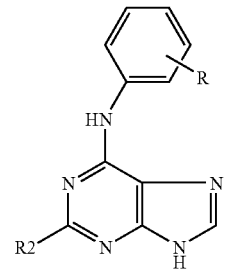

and the pharmaceutically acceptable salts thereof with alkali metals, ammonium or amines, in the form of racemates or optically active isomers, as well as their addition salts with acids, wherein R denotes one to five substituents independently selected from the group comprising hydrogen, halogen, hydroxyl, amino, alkyloxy and alkyl group, R2 is selected from the group comprising amino, halogen, nitro, thio, alkylthio and alkyl group, for use as inhibitors of cytokinin oxidase/dehydrogenase.

The generic substituent groups have meanings identical with the definitions of the corresponding groups as defined in this legend, wherein amino denotes the group —$NH_2$, halogen denotes an atom selected from the group comprising fluorine, bromine, chlorine and iodine atom, nitro denotes the group —$NO_2$, thio denotes the group —SH, alkyl denotes branched or unbranched alkyl group containing 1 to 6 carbon atoms, hydroxy denotes the group —OH, alkyloxy denotes the group —OR, wherein R is alkyl and the said generic substituent groups have meanings identical with the definitions of the corresponding groups as defined in this legend, alkylthio denotes the group —SR, wherein R is alkyl and the said generic substituent groups have meanings identical with the definitions of the corresponding groups as defined in this legend.

In accordance with the invention, preferred substituted 6-anilinopurine derivatives of the general formula I are: 2-(chloro, fluoro, bromo, amino, nitro, thio, methylthio, methyl)-6-anilinopurine, 2-(chloro, fluoro, bromo, amino, nitro, thio, methylthio, methyl)-6-(2-chloroanilino)purine, 2-(chloro, fluoro, bromo, amino, nitro, thio, methylthio, methyl)-6-(3-chloroanilino)purine, 2-(chloro, fluoro, bromo, amino, nitro, thio, methylthio, methyl)-6-(4-chloroanilino)purine, 2-(chloro, fluoro, bromo, amino, nitro, thio, methylthio, methyl)-6-(2-fluoroanilino)purine, 2-(chloro, fluoro, bromo, amino, nitro, thio, methylthio, methyl)-6-(3-fluoroanilino)purine, 2-(chloro, fluoro, bromo, amino, nitro, thio, methylthio, methyl)-6-(4-fluoroanilino)purine, 2-(chloro, fluoro, bromo, amino, nitro, thio, methylthio, methyl)-6-(2-bromoanilino)purine, 2-(chloro, fluoro, bromo, amino, nitro, thio, methylthio, methyl)-6-(3-bromoanilino)purine, 2-(chloro, fluoro, bromo, amino, nitro, thio, methylthio, methyl)-6-(4-bromoanilino)purine, 2-(chloro, fluoro, bromo, amino, nitro, thio, methylthio, methyl)-6-(2-methoxyanilino)

purine, 2-(chloro, fluoro, bromo, amino, nitro, thio, methylthio, methyl)-6-(3-methoxyanilino)purine, 2-(chloro, fluoro, bromo, amino, nitro, thio, methylthio, methyl)-6-(4-methoxyanilino)purine, 2-(chloro, fluoro, bromo, amino, nitro, thio, methylthio, methyl)-6-(2-ethoxyanilino)purine, 2-(chloro, fluoro, bromo, amino, nitro, thio, methylthio, methyl)-6-(3-ethoxyanilino)purine, 2-(chloro, fluoro, bromo, amino, nitro, thio, methylthio, methyl)-6-(4-ethoxyanilino) purine, 2-(chloro, fluoro, bromo, amino, nitro, thio, methylthio, methyl)-6-(2-aminoanilino)purine, 2-(chloro, fluoro, bromo, amino, nitro, thio, methylthio, methyl)-6-(3-aminoanilino)purine, 2-(chloro, fluoro, bromo, amino, nitro, thio, methylthio, methyl)-6-(4-aminoanilino)purine, 2-(chloro, fluoro, bromo, amino, nitro, thio, methylthio, methyl)-6-(2-methylanilino)purine, 2-(chloro, fluoro, bromo, amino, nitro, thio, methylthio, methyl)-6-(3-methylanilino)purine, 2-(chloro, fluoro, bromo, amino, nitro, thio, methylthio, methyl)-6-(4-methylanilino)purine, 2-(chloro, fluoro, bromo, amino, nitro, thio, methylthio, methyl)-6-(2-hydroxyanilino)purine, 2-(chloro, fluoro, bromo, amino, nitro, thio, methylthio, methyl)-6-(3-hydroxyanilino)purine, 2-(chloro, fluoro, bromo, amino, nitro, thio, methylthio, methyl)-6-(4-hydroxyanilino)purine, 2-(chloro, fluoro, bromo, amino, nitro, thio, methylthio, methyl)-6-(2,3-difluoroanilino)purine, 2-(chloro, fluoro, bromo, amino, nitro, thio, methylthio, methyl)-6-(2,4-difluoroanilino)purine, 2-(chloro, fluoro, bromo, amino, nitro, thio, methylthio, methyl)-6-(2,3,4-trifluoroanilino)purine, 2-(chloro, fluoro, bromo, amino, nitro, thio, methylthio, methyl)-6-(2,4,5-trifluoroanilino)purine, 2-(chloro, fluoro, bromo, amino, nitro, thio, methylthio, methyl)-6-(2,3-dichloroanilino)purine, 2-(chloro, fluoro, bromo, amino, nitro, thio, methylthio, methyl)-6-(2,4-dichloroanilino)purine, 2-(chloro, fluoro, bromo, amino, nitro, thio, methylthio, methyl)-6-(2,4-dimethoxyanilino)purine, 2-(chloro, fluoro, bromo, amino, nitro, thio, methylthio, methyl)-6-(2,3-dimethoxyanilino)purine, 2-(chloro, fluoro, bromo, amino, nitro, thio, methylthio, methyl)-6-(3,4-dimethoxyanilino)purine, 2-(chloro, fluoro, bromo, amino, nitro, thio, methylthio, methyl)-6-(2,5-dimethoxyanilino)purine, 2-(chloro, fluoro, bromo, amino, nitro, thio, methylthio, methyl)-6-(3,4,5-trimethoxyanilino)purine, 2-(amino, chloro, fluoro, bromo, amino, nitro, thio, methylthio, methyl)-6-(2,4,6-trimethoxyanilino)purine, 2-(chloro, fluoro, bromo, amino, nitro, thio, methylthio, methyl)-6-(2,3-dimethylanilino)purine, 2-(chloro, fluoro, bromo, amino, nitro, thio, methylthio, methyl)-6-(2,4-dimethylanilino)purine, 2-(chloro, fluoro, bromo, amino, nitro, thio, methylthio, methyl)-6-(3,4-dimethylanilino)purine, 2-(chloro, fluoro, bromo, amino, nitro, thio, methylthio, methyl)-6-(3,5-dimethylanilino)purine, 2-(chloro, fluoro, bromo, amino, nitro, thio, methylthio, methyl)-6-(2,3-dihydroxyanilino)purine, 2-(chloro, fluoro, bromo, amino, nitro, thio, methylthio, methyl)-6-(2,4-dihydroxyanilino)purine, 2-(chloro, fluoro, bromo, amino, nitro, thio, methylthio, methyl)-6-(2,5-dihydroxyanilino)purine, 2-(amino, chloro, fluoro, bromo, amino, nitro, thio, methylthio, methyl)-6-(3,5-dihydroxyanilino)purine, 2-(chloro, fluoro, bromo, amino, nitro, thio, methylthio, methyl)-6-(3-hydroxy-2-methylanilino)purine, 2-(chloro, fluoro, bromo, amino, nitro, thio, methylthio, methyl)-6-(3-hydroxy-4-methylanilino)purine, 2-(chloro, fluoro, bromo, amino, nitro, thio, methylthio, methyl)-6-(2-hydroxy-5-methylanilino)purine, 2-(chloro, fluoro, bromo, amino, nitro, thio, methylthio, methyl)-6-(3-hydroxy-2-methoxyanilino)purine, 2-(chloro, fluoro, bromo, amino, nitro, thio, methylthio, methyl)-6-(3-hydroxy-4-methoxylanilino)purine, 2-(chloro, fluoro, bromo, amino, nitro, thio, methylthio, methyl)-6-(2-hydroxy-3-methoxyanilino)purine, 2-(chloro, fluoro, bromo, amino, nitro, thio, methylthio, methyl)-6-(2-hydroxy-5-methoxylanilino)purine, 2-(chloro, fluoro, bromo, amino, nitro, thio, methylthio, methyl)-6-(4-hydroxy-3,5-dimethoxylanilino)purine, 2-(amino, chloro, fluoro, hydroxy, thio, methylthio, methyl)-6-(2-chloro-4-methoxyanilino)purine, 2-(amino, chloro, fluoro, bromo, nitro, thio, methylthio, methyl)-6-(2-chloro-5-methoxyanilino)purine, 2-(amino, chloro, fluoro, bromo, amino, nitro, thio, methylthio, methyl)-6-(2-chloro-3-methoxyanilino)purine, 2-(chloro, fluoro, bromo, amino, nitro, thio, methylthio, methyl)-6-(2-bromo-3-methoxyanilino)purine, 2-(chloro, fluoro, bromo, amino, nitro, thio, methylthio, methyl)-6-(2-methoxy-3-chloroanilino)purine, 2-(chloro, fluoro, bromo, amino, nitro, thio, methylthio, methyl)-6-(2-methoxy-4-chloroanilino)purine, and the salts thereof with alkali metals, ammonium or amines, in the forms of racemates or optically active isomers, as well as their addition salts with acids, for use as inhibitors of cytokinin oxidase/dehydrogenase.

The following substituted 6-anilinopurine derivatives are particularly preferred, namely:

2-(chloro, fluoro, bromo, amino, nitro, thio, methylthio, methyl)-6-(3-methoxyanilino)purine, 2-(chloro, fluoro, bromo, amino, nitro, thio, methylthio, methyl)-6-(2-hydroxy-3-methoxyanilino)purine, 2-(chloro, fluoro, bromo, amino, nitro, thio, methylthio, methyl)-6-(2-chloro-3-methoxyanilino)purine, 2-(chloro, fluoro, bromo, amino, nitro, thio, methylthio, methyl)-6-(2-bromo-3-methoxyanilino)purine, 2-(chloro, fluoro, bromo, amino, nitro, thio, methylthio, methyl)-6-(4-hydroxyanilino)purine, and the salts thereof with alkali metals, ammonium or amines, in the forms of racemates or optically active isomers, as well as their addition salts with acids, for use as inhibitors of cytokinin oxidase/dehydrogenase.

A further aspect of the invention are pharmaceutical, cosmetic and growth-regulating preparations containing at least one compound of general formula I or the salt thereof with alkali metal, ammonia or amine in the form of racemate or optically active isomer, as well as their addition salts with acids, including excipients.

Another aspect of the invention is the use of substituted 6-anilinopurine derivatives of the general formula I or the salts thereof with alkali metals, ammonium or amines, in the form of racemates or optically active isomers, as well as their addition salts with acids, for the preparation of a composition used for inhibition of cytokinin oxidase/dehydrogenase.

A further aspect of the invention is the use of substituted 6-anilinopurine derivatives of the general formula I as inhibitors of cytokinin oxidase/dehydrogenase, especially for increasing the yield and quality of agricultural products.

A further aspect of the invention is the use of substituted 6-anilinopurine derivatives of the general formula I as inhibitors of cytokinin oxidase/dehydrogenase in tissue cultures for stimulation of proliferation and morphogenesis.

A further aspect of the invention is the use of substituted 6-anilinopurine derivatives of the general formula I as inhibitors of cytokinin oxidase/dehydrogenase for delaying the senescence of plant, mammal, microorganism, yeast and fungal cells.

A further aspect of the invention is the use of substituted 6-anilinopurine derivatives of the general formula I as inhibitors of cytokinin oxidase/dehydrogenase for delaying the senescence of mammalian skin cells, for example fibroblasts and keratinocytes.

A further aspect of the invention is the use of substituted 6-anilinopurine derivatives of the general formula I, for preparation of a composition destined for plant and mammalian embryonic cells and embryos cloning, preferably oocytes cloning.

A further aspect of the invention is the use of substituted 6-anilinopurine derivatives of the general formula I as inhibitors of cytokinin oxidase/dehydrogenase to suppress immunostimulation (e.g. arthritis) or in suppression of transplant rejection in mammals.

A further aspect of the invention is the use of substituted 6-anilinopurine derivatives of the general formula I as inhibitors of cytokinin oxidase/dehydrogenase in the production of crops, in particular cereals (wheat, barley, rice, maize, rye, oat, sorghum, and related species), beet (sugar beet and fodded beet); pomes, drupes and soft fruits (apples, pears, plums, peaches, almonds, cherries, strawberries and blackberries); leguminous plants (beans, lentils, peas, soybeans); oil plants (rape, mustard, poppy, olives, sunflowers, coconut, *Ricinus*, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, *cinnamomum*, camphor) or plants such as tobacco, nuts, eggplants, sugar cane, tea, vine gpapes, hops, bananas and natural rubber and medicinal plants, as well as ornamentals. Crops include those which have been rendered tolerant towards classes of growth factors by conventional breeding methods or genetic engineering methods. The weeds to be controlled can be both monocotyledonous and dicotyledonous weeds, for example *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanbthium, Amaranthus, Chenopodium, Ipomoena, Chrysanthemum, Galium, Viola* and *Veronica*.

The compounds of the general formula I are used in unmodified form or, preferably, together with the excipients conventionally employed in the art of preparations. To this end they are conveniently formulated as concentrates of active compounds as well as suspensions and dispersions, preferentially isotonic water solutions, suspensions and dispersion, diluted emulsions, soluble powders, dusts, granulates, creams, gels, oil suspensions and also encapsulations, e.g. polymeric substances. As with the type of the preparation, the methods of application, such as spraying, atomizing, dusting, scattering, coating or pouring, are chosen in accordance with the intended objectives and the prevailing circumstances. The preparations may be sterilized and/or contain further excipients of neutral nature such as preservatives, stabilizers, wetting agents or emulgators, solubilizing agents, as well as fertilizers, micronutrient donors or other formulations for obtaining special effects.

The compounds of the formula I can be mixed with other growth regulators, resulting in synergistic activities.

PREPARATIONS

The preparations comprising the compounds of general formula I (active ingredients) and, where appropriate, one or more solid or liquid excipients, are prepared in a manner known per se, e.g. by mixing and/or grinding the active ingredients with excipients, e.g. solvents or solid carriers. In addition, surface-active compounds (surfactants) may also be used in the preparations.

Depending on the nature of the compound of general formula I to be formulated, suitable surface-active compounds are non-ionic, cationic and/or anionic surfactants and surfactant mixtures having good emulsifying, dispersing and wetting properties.

Examples of suitable anionic, non-ionic and cationic surfactants are listed, for example, in WO 97/34485.

Also suitable in the preparation of the compositions containing cytokinin oxidase/dehydrogenase inhibitors derived from substituted 6-anilinopurine derivatives according to the invention are the surfactants conventionally used in formulation technology, which are described, inter alia, in "McCutcheon's Detergents and Emulsifiers Annual" MC Publishing Corp., Ridgewood N.J., 1981; Stache, H., "Tensid-Taschenbuch", Carl Hanser Verlag, Munich, 1981; and M. and J. Ash, "Encyclopedia of Surfactants", Vol. 1-3, Chemical Publishing Co., New York, 1980-81.

The formulation of the preparation containing cytokinin oxidase/dehydrogenase inhibitors usually contains from 0.1 to 95% active ingredient by weight, from 5 to 99.9% by weight of solid or liquid adjuvants or pharmaceutical carriers, depending on the application method, and from 0.1 to 25% by weight of a surfactant.

Whereas commercial products are usually formulated as concentrates, the end user will normally employ dilute formulations. The compositions may also comprise further ingredients, such as stabilisers, e.g. vegetable oils or epoxidised vegetable oils (epoxidised coconut 0;1, rapeseed oil or soybean oil), antifoams, e.g. silicone oil, preservatives, stabilizers, wetting agents or emulsifiers, viscosity factors, binders, tackifiers, and also fertilisers or other active ingredients. Preferred formulations have especially the following compositions: (%=percent by weight)

Emulsifiable Concentrates:

| | |
|---|---|
| active ingredient mixture: | 1 to 90%, preferably 5 to 20% |
| surfactant: | 1 to 30%, preferably 10 to 20% |
| liquid carrier: | 5 to 94%, preferably 70 to 85% |

Dusts:

| | |
|---|---|
| active ingredient mixture: | 0.1 to 10%, preferably 0.1 to 5% |
| solid carrier: | 99.9 to 90%, preferably 99.9 to 95% |

Suspension Concentrates:

| | |
|---|---|
| active ingredient mixture: | 5 to 75%, preferably 10 to 50% |
| water: | 94 to 24%, preferably 88 to 30% |
| surfactant: | 1 to 40%, preferably 2 to 30% |

Wettable Powders:

| | |
|---|---|
| active ingredient mixture: | 0.5 to 90%, preferably 1 to 80% |
| surfactant: | 0.5 to 20%, preferably 1 to 15% |
| solid carrier: | 5 to 95%, preferably 15 to 90% |

Granules:

| | |
|---|---|
| active ingredient mixture: | 0.1 to 30%, preferably 0.1 to 15% |
| solid carrier: | 99.9 to 70%, preferably 99.9 to 85% |

The compositions may also comprise further ingredients, such as stabilisers, e.g. vegetable oils or epoxidised vegetable oils (epoxidised coconut oil, rapeseed oil or soybean oil), anti-foams, e.g. silicone oil, preservatives, viscosity regulators, binders, tackifiers, and also fertilisers or other active ingredients. For the use of the compounds of general formula I, or of compositions comprising them, in the protection of crop plants against the damaging effects of growth regulators, various methods and techniques come into consideration, such as, for example, the following:

i) Seed Dressing a) Dressing of the seeds with a wettable powder formulation of a compound of the general formula I by shaking in a vessel until uniformly distributed over the seed surface (dry dressing). In that procedure approximately from 1 to 500 g of compound of the general formula I (4 g to 2 kg of wettable powder) are used per 100 kg of seed.

b) Dressing of the seeds with an emulsifiable concentrate of a compound of formula I according to method a) (wet dressing).

c) Dressing by immersing the seeds for from 1 to 72 hours in a liquor comprising from 100 to 1000 ppm of a compound of general formula I and preferably subsequently drying the seeds (immersion dressing).

Dressing the seeds or treating the germinated seedlings are naturally the preferred methods of application, because treatment with the active ingredients is directed entirely at the target crop. Generally from 1 to 1000 g of antidote, preferably from 5 to 250 g of antidote, are used per 100 kg of seed, but depending on the methodology, which also enables the addition of other active ingredients or micronutrients: the concentration limits indicated can be varied up or down (repeat dressing).

ii) Application as a Tank Mixture

A liquid formulation of a mixture of antidote and growth regulator is used (ratio by weight of the one to the other from 10:1 to 1:100), the rate of application of growth regulator being from 0.005 to 5.0 kg per hectare. Such tank mixtures are applied before or after sowing.

iii) Application to the Seed Furrow

The compounds of formula I are introduced into the open, sown seed furrow in the form of an emulsifiable concentrate, wettable powder or granules. Once the seed furrow has been covered over, the growth regulator is applied in the usual manner in the pre-emergence process.

iv) Controlled Release of Active Ingredient

The compounds of formula I are applied in solution to mineral granule carriers or polymerised granules (urea/formaldehyde) and dried. If desired, it is also possible to apply a coating that allows the active ingredient to be released in metered amounts over a specific period of time (coated granules).

The cosmetic compositions comprise from about 0.05% (w/w) to about 10% (w/w) of the active ingredient, preferably from about 0.1% (w/w) to about 2% (w/w). The cosmetic compositions are in the form of a cream, an aerosol, a milky lotion, a lotion, a plaster, a poultice, a shampoo, a lipstick, a paste, an ointment, a paste, a tincture, a spray etc.

Ointments are oil-in-water emulsions, which comprise not more than 70%, but preferably 20-50% of water or aqueous phase. The fatty phase consists of, in particular, hydrocarbons, for example vaseline, paraffin oil or hard paraffins, which preferably comprise suitable hydroxy compounds, such as fatty alcohols or esters thereof, for example cetyl alcohol or wool wax alcohols, such as wool wax, to improve the water-binding capacity. Emulsifiers are lipophilic substances, such as sorbitan fatty acid esters (Spans), preferably sorbitan oleate or sorbitan isostearate. Additives to the aqueous phase are, for example, humectants, such as polyalcohols, for example glycerol, propylene glycol, sorbitol and polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or hydrogenated oils, for example hydrogenated groundnut or castor oil, and furthermore fatty acid partial esters of glycerol, for example glycerol mono- and distearate. They also contain e.g. fatty alcohols, emulsifiers and additives mentioned in connection with ointments which increase the uptake of water.

Creams are oil-in-water emulsions, which comprise more than 50% of water. Oily bases used are, in particular, fatty alcohols, for example isopropyl myristate, wool wax, beeswax, or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof, such as polyglyceric fatty acid esters or polyethylene sorbitan fatty acid esters or acidic polyglyceric fatty acid esters (Tween), and furthermore polyoxyethylene fatty alcohol ethers or polyoxyethylene fatty acid esters, or ionic emulsifiers, such as alkali metal salts of fatty alcohol sulphates, preferably sodium lauryl sulphate, sodium cetyl sulphate or sodium stearyl sulphate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and polyethylene glycols, and furthermore preservatives and odoriferous substances.

Pastes are creams or ointments containing secretion-absorbing powder constituents, such as metal oxides, for example titanium oxide or zinc oxide, and in addition talc or aluminium silicates, which have the task of binding the moisture or secretions present.

Suspensions in oil comprise, as the oily component, the vegetable, synthetic or semisynthetic oils, commonly used for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidonic acid, behenic acid or corresponding unsaturated acids, for example oleic acid, elaidic acid, euric acid, brasidic acid and linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefosé, Paris), "Labrafil M 1944 CS" (unsaturated polyglycolated glycerides prepared by an alcoholysis of apricot kernel oil and made up of glycerides and polyethylene glycol esters; from Gattefose, Paris), "Labrasol" (saturated polyglycolated glycerides prepared by an alcoholysis of TCM and made up of glycerides and polyethylene glycol esters; from Gattefosé, Paris), "Miglyol 812" (triglyceride of saturated fatty acids of chain length $C_8$ to $C_{12}$ from Hüls AG, Germany), and in particular vegetable oils, such as cottonseed oil, almond oil, olive oil, castor oil, sesame oil, soybean oil and groundnut oil.

Foams are administered from pressurised containers and they are liquid oil-in-water emulsions present in aerosol foam. As the propellant gases halogenated hydrocarbons, such as polyhalogenated alkanes, for example dichlorofluoromethane and dichlorotetrafluoroethane, or, preferably, non-halogenated gaseous hydrocarbons, air, $N_2O$, or carbon dioxide are used. The oily phases used are, inter alia, those mentioned above for ointments, and the additives mentioned there are likewise used.

Tinctures and solutions usually comprise an aqueous-ethanolic base to which, humectants for reducing evaporation, such as polyalcohols, for example glycerol, glycols and polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives are admixed.

EXAMPLES OF CARRYING OUT THE INVENTION

Figure 1:
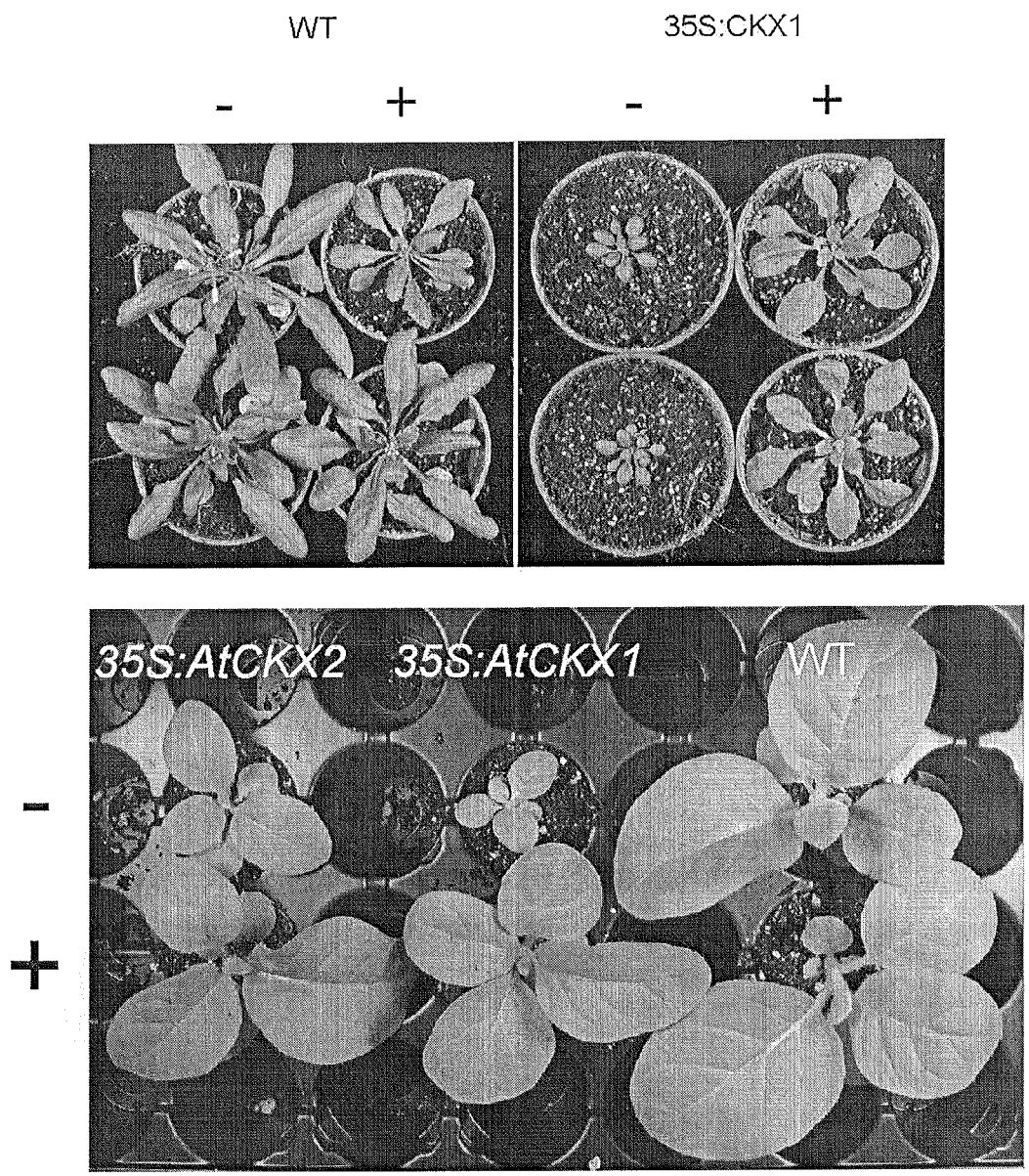
FIG. 1 shows complementation of wild-type phenotype after systematic treatment of CKX overproducing plants by compound 12. + means treated, − means not treated.

The starting material for the compounds of the formula I is 2,6-dichloropurine. Another starting material can be 2-amino-6-chloropurine or 2-fluoro-6-chloropurine, synthesised from 2-amino-6-chloropurine by reaction with tetrafluoroboric acid in the presence of sodium nitrate aqueous solution (Beach et al., 1992). Another starting compound, 2-bromo-6-chloropurine, can be prepared from 2-amino-6-chloropurine by diazotation with t-butyl nitrite and subsequent bromination in the presence of a suitable bromine donor (Kim Hak Sung et al.; J. Med. Chem. 46; 23; 2003; 4974-4987). Yet another starting material can be 2-methyl-6-chloropurine, which can be prepared from 6-chloro-2-iodopurine by Stille's cross coupling (Kim et al., 2003). Yet another starting material can be 2-nitro-6-chloro-9-Boc-purine, which can be prepared from 6-chloropurine (Rodenko et al.; J. Am. Chem. Soc. 2005, 127, 5957-5963).

Starting substituted phenylamines, not commercially available (others obtained via Sigma Aldrich or Fluorochem), were prepared from the corresponding aldehydes in the presence of suitable catalyst. These, which have more hydroxyl groups, may also be prepared by demethylation of appropriate methoxy derivatives using 48% HBr in $N_2$ atmosphere.

Elemental analyses (C, H and N) were performed on an EA1108 CHN analyser (Fissons Instruments). The melting points were determined on a BÜCHI Melting Point B-540 apparatus. Analytical thin layer chromatography (TLC) was carried out using silica gel 60 $WF_{254}$ plates (Merck), mobile phase $CHCl_3$:MeOH:conc. $NH_4OH$ (8:2:0.2, v/v/v). ES+ mass spectra were recorded using direct probe on Waters ZMD 2000 mass spectrometer. The mass monitoring interval was 10-1500 amu. The spectra were collected using 3.0 second cyclical scans and applying sample cone voltage 25 V at source block temperature 150° C., desolvation temperature 80° C. and desolvation gas flow rate 200 l/hour. The mass spectrometer was directly coupled to a MassLynx data system. NMR spectra were measured in a Bruker Avance AV 300 spectrometer operating at a temperature of 300 K and a frequency of 300.13 MHz ($^1H$) and 75.48 MHz ($^{13}C$), respectively. Samples were prepared by dissolving the compounds in DMSO-$d_6$. Tetramethylsilane (TMS) was used as the internal standard.

Example 1

2-Chloro-6-anilinopurine

Aniline (4.66 g; 0.05 mol) was added to a suspension of 2,6-dichloropurine (5.67 g; 0.03 mol) in n-propanol (60 ml) and N,N-ethyldiisopropylamine (6.44 g; 0.05 mol) was added. The reaction mixture was stirred at 100° C. for 4 hours. After cooling to room temperature the precipitate was filtered off, washed with n-propanol (2×10 ml) and water (3×10 ml) and dried in the drying oven at 60° C. into constant weight. Yield: 6.26 g yellowish substance (84.9%). TLC (chloroform-methanol; 85:15): one single spot; free of the starting material, HPLC purity: 98+%

Example 2

2-Chloro-6-(3-chloroanilino)purine 2,6-Dichloropurine (3.78 g; 0.02 mol) was reacted with 3-chloroaniline (3.83 g; 0.03 mol) in n-butanol (40 ml) in the presence of triethylamine (7 ml; 0.05 mol) at 110° C. for 3 hours. After cooling to room temperature the reaction mixture was stirred at 0° C. for 2 hours. The yellow precipitate was filtered off, washed with cold n-butanol (2×10 ml), water (3×10 ml) and dried in the drying oven at 60° C. into constant weight. Yield: 3.69 g yellow crystalline powder (65.8%). The crude product was crystallized from isopropanol to give 2.85 g of pure substance. TLC (chloroform-methanol; 85:15): one single spot; free of starting material. HPLC purity: 98+%

Example 3

2-Chloro-6-(3-fluoroanilino)purine

This compound was prepared in a similar manner as described in example 2, by reaction of 2,6-dichloropurine with 3-fluoroaniline. The reaction mixture was then evaporated on a rotary vacuum evaporator and the residue was partitioned between ethyl acetate and 0.5 M HCl. The organic layer was washed with water, dried with $MgSO_4$, and evaporated to give a yellow solid (3.72 g). The crude product was purified by flash chromatography. Yield: 2.20 g yellow crystalline powder. TLC (chloroform-methanol; 85:15): homogenous. HPLC purity: 98+%

Example 4

2-Chloro-6-(3-hydroxyanilino)purine

This compound was prepared by the reaction of 2,6-dichloropurine (3.78 g; 0.02 mol), 3-aminophenol (3.27 g; 0.03 mol), and N,N-ethyldiisopropylamine (6.44 g; 0.05 mol) in n-butanol (40 ml) at 90° C. for 4 hours. The reaction mixture was then allowed to cool to room temperature and stirred. The formed crystalline precipitate was collected, rinsed with cold n-butanol (3×10 ml), water (3×10 ml) and dried in the oven into constant weight.

TLC (chloroform-methanol; 85:15): homogenous. HPLC purity: 98+%

Example 5

2-Chloro-6-(3-methoxyanilino)purine

To a suspension of 2,6-dichloropurine (3.78 g; 0.02 mol) and m-anisidine (3.69 g; 0.03 mol) in n-pentanol (40 ml), triethylamine (7 ml; 0.05 mol) was added. The reaction mixture was stirred at 100° C. for 4 hours and then it was allowed to cool to the room temperature. The white precipitate was collected, washed with isopropanol (2×10 ml) and water (3×10 ml). The crude product was purified by the crystallization from methanol in the presence of activated charcoal to give white crystals. Yield: 4.36 g (77.8%). TLC (chloroform-methanol; 85:15): one single spot, free of starting material, HPLC purity: 98+%

TABLE 1

Compounds Prepared by the methods of Examples 1-5

| | PURINE SUBSTITUENT | | CHN ANALYSES | MS ANALYSES-ZMD | |
|---|---|---|---|---|---|
| | R6 | R2 | [%] | $[M-H]^-$ a) | $[M+H]^+$ b) |
| 1 | anilino | chloro | C = 53.5; H = 3.3; N = 28.6 | 244 | 246 |
| 2 | 2-chloroanilino | chloro | C = 46.8; H = 2.9; N = 24.7 | 278 | 280 |
| 3 | 3-chloroanilino | chloro | C = 46.8; H = 2.9; N = 24.6 | 278 | 280 |
| 4 | 4-chloroanilino | chloro | C = 46.9; H = 3.0; N = 24.7 | 278 | 280 |
| 5 | 2-fluoroanilino | chloro | C = 49.9; H = 3.0; N = 26.5 | 262 | 264 |
| 6 | 3-fluoroanilino | chloro | C = 49.7; H = 3.0; N = 26.7 | 262 | 264 |
| 7 | 4-fluoroanilino | chloro | C = 49.8; H = 3.1; N = 26.4 | 262 | 264 |
| 8 | 2-hydroxyanilino | chloro | C = 49.7; H = 3.1; N = 26.7 | 260 | 262 |
| 9 | 3-hydroxyanilino | chloro | C = 49.9; H = 3.2; N = 26.7 | 260 | 262 |
| 10 | 4-hydroxyanilino | chloro | C = 50.5; H = 3.1; N = 26.8 | 260 | 262 |
| 11 | 2-methoxyanilino | chloro | C = 51.4; H = 3.8; N = 25.5 | 274 | 276 |
| 12 | 3-methoxyanilino | chloro | C = 51.8; H = 3.8; N = 25.2 | 274 | 276 |
| 13 | 4-methoxyanilino | chloro | C = 52.0; H = 3.7; N = 25.2 | 274 | 276 |
| 14 | 2-aminoanilino | chloro | C = 50.5; H = 3.2; N = 32.8 | 259 | 261 |
| 15 | 3-aminoanilino | chloro | C = 50.6; H = 3.2; N = 32.5 | 259 | 261 |
| 16 | 4-aminoanilino | chloro | C = 50.4; H = 3.3; N = 32.3 | 259 | 261 |
| 17 | 3,4-dimethoxyanilino | chloro | C = 51.3; H = 3.9; N = 23.3 | 304 | 306 |
| 18 | 2,5-dimethoxyanilino | chloro | C = 51.3; H = 4.0; N = 23.2 | 304 | 306 |
| 19 | 3,4,5-trimethoxyanilino | chloro | C = 49.9; H = 4.2; N = 21.0 | 334 | 336 |
| 20 | 3,4-dihydroxyanilino | chloro | C = 47.2; H = 2.8; N = 25.5 | 276 | 278 |
| 21 | 2,5-dihydroxyanilino | chloro | C = 47.3; H = 2.8; N = 25.6 | 276 | 278 |
| 22 | 2-chloro-5-methoxyanilino | chloro | C = 46.3; H = 2.9; N = 22.7 | 308 | 310 |
| 23 | 2-chloro-3-methoxyanilino | chloro | C = 46.4; H = 2.9; N = 22.7 | 308 | 310 |
| 24 | 2-bromo-3-methoxyanilino | chloro | C = 40.8; H = 2.5; N = 19.4 | 353 | 355 |
| 25 | 2-methoxy-3-chloroanilino | chloro | C = 46.4; H = 3.0; N = 22.6 | 308 | 310 |
| 26 | 3-ethoxyanilino | chloro | C = 53.8; H = 4.1; N = 24.3 | 288 | 290 |
| 27 | 2-hydroxy-5-methylanilino | chloro | C = 51.9; H = 3.6; N = 25.7 | 274 | 276 |
| 28 | 3-hydroxy-4-methylanilino | chloro | C = 52.1; H = 3.7; N = 25.5 | 274 | 276 |
| 29 | 3-hydroxy-2-methylanilino | chloro | C = 52.1; H = 3.8; N = 25.4 | 274 | 276 |
| 30 | 3,4-dimethylanilino | chloro | C = 56.8; H = 4.1; N = 25.7 | 272 | 274 |
| 31 | 2-hydroxy-3-methoxyanilino | chloro | C = 49.3 H = 3.6; N = 24.3 | 290 | 292 |
| 32 | 2-hydroxy-4-methoxyanilino | chloro | C = 49.2; H = 3.7; N = 24.7 | 290 | 292 |
| 33 | 4-hydroxy-3,5-dimethoxyanilino | chloro | C = 48.2; H = 3.6; N = 21.9 | 320 | 322 |
| 34 | 2,3-difluoroanilino | chloro | C = 46.6; H = 2.0; N = 25.1 | 280 | 282 |
| 35 | 2,4-difluoroanilino | chloro | C = 46.7; H = 2.0; N = 25.1 | 280 | 282 |
| 36 | 2,3,4-trifluoroanilino | chloro | C = 43.6; H = 1.6; N = 23.7 | 280 | 282 |
| 37 | 2,4,5-trifluoroanilino | chloro | C = 43.8; H = 1.6; N = 23.6 | 280 | 282 |
| 38 | 2,3-dichloroanilino | chloro | C = 42.3; H = 2.0; N = 22.0 | 312 | 314 |
| 39 | 2,4-dichloroanilino | chloro | C = 42.0; H = 2.0; N = 22.2 | 312 | 314 |

Example 6

2-Amino-6-(3-methoxyanilino)purine

To a suspension of 2-amino-6-chloropurine (1.69 g; 0.01 mol) and m-anisidine (1.23 g; 0.01 mol) in n-butanol (20 ml), triethylamine (3.5 ml; 0.025 mol) was added. The resulting thick suspension was stirred at 110° C. for 3 hours. The TLC showed the absence of the starting material and the presence of the desired product. The reaction mixture was then cooled to room temperature. The white precipitate was filtered off, rinsed with n-butanol (3×10 ml) and water (3×10 ml) and dried in the drying oven into constant weight. Yield: 2.19 g (85%). The crude product was purified as hydrochloride salt by crystallization from 2.5 M methanolic hydrogen chloride to give 2.17 g of almost white crystals (as hydrochloride). TLC (chloroform-methanol-$NH_4OH$; 4:1:0.05): one single spot, free of starting material. HPLC purity: 99+%.

TABLE 2

Compounds Prepared by the Method of Example 6

| | PURINE SUBSTITUENT | | CHN ANALYSES | MS ANALYSES-ZMD | |
|---|---|---|---|---|---|
| | R6 | R2 | [%] | $[M - H]^-$ a) | $[M + H]^+$ b) |
| 40 | anilino | fluoro | C = 57.6; H = 3.5; N = 30.7 | 228 | 230 |
| 41 | 2-chloroanilino | fluoro | C = 49.7; H = 2.7; N = 26.8 | 262 | 264 |
| 42 | 3-chloroanilino | fluoro | C = 49.9; H = 2.7; N = 26.7 | 262 | 264 |
| 43 | 4-chloroanilino | fluoro | C = 50.0; H = 2.7; N = 26.7 | 262 | 264 |
| 44 | 2-fluoroanilino | fluoro | C = 53.4; H = 2.7; N = 28.5 | 246 | 248 |
| 45 | 3-fluoroanilino | fluoro | C = 53.3; H = 2.7; N = 28.5 | 246 | 248 |
| 46 | 4-fluoroanilino | fluoro | C = 53.4; H = 2.8; N = 28.4 | 246 | 248 |
| 47 | 2-hydroxyanilino | fluoro | C = 53.0; H = 3.4; N = 28.3 | 244 | 246 |
| 48 | 3-hydroxyanilino | fluoro | C = 53.4; H = 3.4; N = 28.2 | 244 | 246 |
| 49 | 4-hydroxyanilino | fluoro | C = 53.9; H = 3.3; N = 28.5 | 244 | 246 |
| 50 | 2-methoxyanilino | fluoro | C = 54.7; H = 4.1; N = 27.0 | 258 | 260 |
| 51 | 3-methoxyanilino | fluoro | C = 55.1; H = 4.0; N = 26.9 | 258 | 260 |
| 52 | 4-methoxyanilino | fluoro | C = 55.0; H = 4.0; N = 27.4 | 258 | 260 |
| 53 | 3,4-dimethoxyanilino | fluoro | C = 53.7; H = 3.9; N = 24.8 | 288 | 290 |
| 54 | 2,5-dimethoxyanilino | fluoro | C = 53.6; H = 4.0; N = 24.5 | 288 | 290 |
| 55 | 3,4-dihydroxyanilino | fluoro | C = 50.2; H = 3.0; N = 27.3 | 260 | 262 |
| 56 | 2,5-dihydroxyanilino | fluoro | C = 50.2; H = 3.0; N = 27.2 | 260 | 262 |
| 57 | 2-chloro-5-methoxyanilino | fluoro | C = 49.0; H = 3.1; N = 24.0 | 292 | 294 |
| 58 | 2-methoxy-3-chloroanilino | fluoro | C = 48.0; H = 3.0; N = 24.0 | 292 | 294 |
| 59 | 3-ethoxyanilino | fluoro | C = 56.8; H = 4.2; N = 26.0 | 272 | 274 |
| 60 | 2-hydroxy-5-methylanilino | fluoro | C = 55.2; H = 3.8; N = 27.2 | 258 | 260 |
| 61 | 3-hydroxy-4-methylanilino | fluoro | C = 55.3; H = 3.8; N = 27.2 | 258 | 260 |
| 62 | 3-hydroxy-2-methylanilino | fluoro | C = 55.3; H = 3.9; N = 27.0 | 258 | 260 |
| 63 | 3,4-dimethylanilino | fluoro | C = 60.4; H = 4.6; N = 27.4 | 256 | 258 |

Example 7

2-Fluoro-6-(3-methoxyanilino)purine

This compound was prepared by the reaction of 2-fluoro-6-chloropurine (1.7 g; 0.01 mol), m-anisidine (1.23 g; 0.01 mol) and triethylamine (3.5 ml; 0.025 mol) in n-butanol (20 ml) at 90° C. for 4 hours. The reaction mixture was then cooled to the room temperature. The white precipitate was filtered off, rinsed with n-butanol (3×10 ml) and water (3×10 ml) and dried in the drying oven into constant weight. Yield: 5.55 g (61%) of yellowish crystalline powder. TLC (chloroform-methanol; 85:15): one single spot. HPLC purity: 99+%.

TABLE 3

Compounds Prepared by the Method of Example 7

| | PURINE SUBSTITUENT | | CHN ANALYSES | MS ANALYSES-ZMD | |
|---|---|---|---|---|---|
| | R6 | R2 | [%] | $[M - H]^-$ a) | $[M + H]^+$ b) |
| 64 | anilino | amino | C = 58.2; H = 4.4; N = 37.5 | 225 | 227 |
| 65 | 2-chloroanilino | amino | C = 50.2; H = 3.3; N = 32.9 | 259 | 261 |
| 66 | 3-chloroanilino | amino | C = 50.5; H = 3.4; N = 32.6 | 259 | 261 |
| 67 | 4-chloroanilino | amino | C = 50.5; H = 3.4; N = 32.5 | 259 | 261 |
| 68 | 2-fluoroanilino | amino | C = 53.8; H = 3.7; N = 34.7 | 243 | 245 |
| 69 | 3-fluoroanilino | amino | C = 53.9; H = 3.6; N = 34.8 | 243 | 245 |
| 70 | 4-fluoroanilino | amino | C = 54.0; H = 3.7; N = 34.5 | 243 | 245 |
| 71 | 2-hydroxyanilino | amino | C = 54.0; H = 4.1; N = 34.9 | 241 | 243 |

TABLE 3-continued

Compounds Prepared by the Method of Example 7

| PURINE SUBSTITUENT | | CHN ANALYSES | MS ANALYSES-ZMD | |
|---|---|---|---|---|
| R6 | R2 | [%] | [M − H]− a) | [M + H]+ b) |
| 72 3-hydroxyanilino | amino | C = 54.1; H = 4.2; N = 34.8 | 241 | 243 |
| 73 4-hydroxyanilino | amino | C = 54.4; H = 4.2; N = 34.7 | 241 | 243 |
| 74 2-methoxyanilino | amino | C = 55.9; H = 4.7; N = 33.0 | 255 | 257 |
| 75 3-methoxyanilino | amino | C = 56.0; H = 4.8; N = 32.9 | 255 | 257 |
| 76 4-methoxyanilino | amino | C = 56.3; H = 4.7; N = 32.9 | 255 | 257 |
| 77 3,4-dimethylanilino | amino | C = 51.0; H = 5.5; N = 33.4 | 253 | 255 |

Example 8

2-Thioxanthine 4,5-Diamino-6-hydroxy-2-thiopyrimidine (MW 158, Aldrich 95%, 100 g) was refluxed with 90% formic acid (500 ml) for 2 h with mechanical stirring. The mix initially solidifies and a further 100 ml of formic acid is added. The mixture was cooled to 1° C. on ice and then filtered to get crude 4-amino-5-formamido-6-hydroxy-2-thiopyrimidine which is dried under vacuum for 30 min The filter cake was re-suspended in formamide (225 ml) and heated to 175-185° C. in a liquid paraffin bath with occasional hand stirring for 2 h. Subsequently, the reaction mixture was cooled to the room temperature and filtered. It was dissolved in approx. 2 L 1 M NaOH, filtered, and vacuum dried at 95° C. for 2 h. Yield 103 g (97%).

Example 9

2-Benzylthio-6-purinol 5.28 g 8-thioxanthine was suspended in 78.5 ml of 1 M NaOH and diluted to approx. 400 ml with water. (The starting material does not completely dissolve even with the 2.5-fold excess of the base.) 3.7 ml of benzyl chloride was then added in a single portion and the mixture vigorously stirred for approx. 3 h at the room temperature, then pH adjusted to 5 with glacial AcOH to yield a red precipitate, which was filtered, washed thoroughly with water and dried overnight in vacuo at 80° C. to give 7.33 g of a salmon-pink solid which was used without further purification.

Example 10

2-Benzylthio-6-chloropurine

2-Benzylthioxanthine (27.6 g, 0.107 mmol) was covered with $POCl_3$ (506 ml) and N,N-diethylaniline (40 ml) was added. The mixture was refluxed for 1.5 h. Excess oxychloride was removed in vacuo to give a syrup which was poured onto ice (2 kg). Sodium hydroxide was added, with cooling, to dissolve the solid formed. The mixture was acidified to pH 1 with concentrated HCl to give a solid which was filtered off, washed with water and dried in vacuo at 70° C. for several hours. The crude product, powdered, was mixed with a small amount of methanol and the yellow solid was dried in vacuo at 70° C. for several hours. Yield 17.5 g (59%). Crude 2-benzylthio-6-chloropurine and 2-benzylthioxanthine dissolve readily in DMSO. TLC (chloroform/MeOH; v/v): without starting material. Crude product chromatographically purified over 125 g silica packed and eluted with 2.5% MeOH/chloroform. Product elutes 7 to 36 were dried to a yellow solid and the chromatography-purified product recrystallized from 50% aqueous MeOH. The yield was white solid and it was dried to constant weight over calcium chloride followed by phosphorus pentoxide at 45° C. overnight. Yield: 3 g. M.p. 176-178° C., sharp, no decomposition. TLC (SILICA-5% MeOH/chloroform). Single, sharp major spot (0.53). HPLC purity: 95+%

Example 11

2-Benzylthio-6-anilinopurine

2-Benzylthio-6-chloropurine (3.9 g) and aniline (3.42 g) in n-BuOH (100 ml) in the presence of triethylamine (7.5 ml) were refluxed for 2 h. Reaction mixture was cooled to room temperature, dried at a rotary vacuum evaporator, cooled with ice and 400 ml water was added with vigorous shaking. At standing overnight at −16° C. crude dark-brown solid was formed, which was dried into constant weight and chromatographically purified over 100 g silica packed in chloroform. The column was eluted with 500 ml 100% chloroform followed by 500 ml 1.25% MeOH/chloroform and then 1.5 L 2.5% MeOH/chloroform; 100 ml fractions collected and fractions 12 to 15 were dried to yield light-brown solid which were recrystallized from MeOH in the presence of active carbon. Yield 1.18 g of white, amorphous solid. TLC (2.5% MeOH/chloroform) shows only a single spot with no contaminants. HPLC purity: 98+%.

Example 12

2-Thio-6-anilinopurine

2-Benzylthio-6-anilinopurine (1.18 g) was dissolved in liquid ammonia (125 ml). Sodium was added in small portions until a persisting blue colouration. A small amount of solid ammonium chloride was added cautiously to remove excess Na. The ammonia was evaporated to a small volume on a hot plate and ether (125 ml) added. Most of the remaining ammonia was extracted with water (2×65 ml). The pH of aqueous extract was adjusted to 5 with AcOH followed by cooling to below −10° C. on dry ice. A creamy solid precipitated. The solid was filtered, washed thoroughly with water and dried overnight over calcium chloride to yield a virtually white powder. Yield 760 mg. TLC: no contaminants. HPLC purity: 95%.

TABLE 4

Compounds Prepared by the Method of Example 12

| | PURINE SUBSTITUENT | | CHN ANALYSES | MS ANALYSES-ZMD | |
|---|---|---|---|---|---|
| | R6 | R2 | [%] | [M − H]− a) | [M + H]+ b) |
| 78 | anilino | Thio | C = 54.0; H = 3.5; N = 29.0 | 242 | 244 |
| 79 | 2-chloroanilino | Thio | C = 47.2; H = 2.7; N = 25.4 | 276 | 278 |
| 80 | 3-chloroanilino | Thio | C = 47.4; H = 2.8; N = 25.1 | 276 | 278 |
| 81 | 4-chloroanilino | Thio | C = 47.4; H = 2.8; N = 25.2 | 276 | 278 |
| 82 | 2-fluoroanilino | Thio | C = 50.5; H = 3.0; N = 27.0 | 260 | 262 |
| 83 | 3-fluoroanilino | Thio | C = 50.5; H = 2.8; N = 27.0 | 260 | 262 |
| 84 | 4-fluoroanilino | Thio | C = 50.4; H = 3.0; N = 27.2 | 260 | 262 |
| 85 | 2-hydroxyanilino | Thio | C = 50.6; H = 3.4; N = 27.2 | 258 | 260 |
| 86 | 3-hydroxyanilino | Thio | C = 50.2; H = 3.2; N = 27.7 | 258 | 260 |
| 87 | 2-methoxyanilino | Thio | C = 52.5; H = 4.0; N = 26.0 | 272 | 274 |
| 88 | 3-methoxyanilino | Thio | C = 52.6; H = 4.1; N = 25.7 | 272 | 274 |
| 89 | 4-methoxyanilino | Thio | C = 52.5; H = 4.0; N = 25.9 | 272 | 274 |
| 90 | 3,4-dimethoxyanilino | Thio | C = 51.7; H = 4.1; N = 23.5 | 302 | 304 |
| 91 | 2,5-dimethoxyanilino | Thio | C = 51.1; H = 4.3; N = 23.3 | 302 | 304 |
| 92 | 2-chloro-5-methoxyanilino | Thio | C = 46.3; H = 3.1; N = 22.9 | 306 | 308 |
| 93 | 2-methoxy-3-chloroanilino | Thio | C = 46.4; H = 3.2; N = 22.9 | 306 | 308 |

Example 13

2-Methylthioxanthine

To a freshly prepared solution of 2-Thioxanthine (103 g, 0.613 mol) was dissolved in 2 M NaOH (613 ml) and water (245 ml), dimethyl sulphate (77 g, 58 ml) was added dropwise, keeping temperature between 25 and 40° C. The reaction mixture was stirred for 1 h and left to stand at room temperature overnight. Then the dark-red liquid was filtered and the product was precipitated with glacial acetic acid. After filtration the solid was re-crystallised from boiling water (1500 ml). The product crystallized at −10° C., was filtered and vacuum dried at 95° C. for 3 h, then to constant weight over phosphorus pentoxide. Yield: 48 g. HPLC purity: 80%.

Example 14

2-Methylthio-6-chloropurine

2-Methylthioxanthine (65 g) was mixed with $POCl_3$ (975 ml) and N,N-diethylaniline (97.5 ml). The mixture was refluxed with mechanical stirring for 90 min Excess $POCl_3$ was removed in vacuo with rotary vacuum evaporator at 55-60° C. and the residue poured onto ice (0° C., 1.75 kg). The mixture was stirred for 10 min to complete hydrolysis of the $POCl_3$ and extracted with ethyl acetate (4×2.5 l). The combined ethyl acetate extracts were washed with water and dried to give a dark solid. The crude solid was recrystallised with decolourisation by active carbon from ethanol and dried to constant weight over phosphorus pentoxide. Yield 23.6 g (33%). HPLC purity: 99%. TLC (chloroform/methanol, 9/1) without impurities.

Example 15

2-Methylthio-6-anilinopurine 2-methylthio-6-chloropurine (10 g, 50 mmol), aniline (7.7 g, 63 mmol) and triethylamine (35 ml, 250 mmol) were refluxed in butanol (400 ml) for 2 h. Butanol was removed in vacuo and water (290 ml) added to the cooled residue. pH was adjusted to 8.0, the mixture was left at −16° C. overnight. Filtration and drying over phosphorus pentoxide in vacuo gave 10 g crude yellow-green product. The product was chromatographically purified (250 g silica, Fisons, chloroform); eluted with chloroform/methanol (97/3, v/v). Appropriate fractions were dried in vacuo, re-crystallised from ethanol with decolourisation by active carbon. After drying to constant weight over $P_2O_5$, yield 5.76 g, (46%), HPLC purity >98%. TLC: chloroform/methanol (9/1, v/v), no contaminants.

TABLE 5

Compounds Prepared by the Method of Example 15

| | PURINE SUBSTITUENT | | CHN ANALYSES | MS ANALYSES-ZMD | |
|---|---|---|---|---|---|
| | R6 | R2 | [%] | [M − H]− a) | [M + H]+ b) |
| 94 | anilino | methylthio | C = 55.9; H = 4.2; N = 27.3 | 256 | 258 |
| 95 | 2-chloroanilino | methylthio | C = 49.1; H = 3.3; N = 24.3 | 290 | 292 |
| 96 | 3-chloroanilino | methylthio | C = 49.1; H = 3.1; N = 24.1 | 290 | 292 |
| 97 | 2-fluoroanilino | methylthio | C = 52.2; H = 3.7; N = 25.3 | 274 | 276 |
| 98 | 3-fluoroanilino | methylthio | C = 52.4; H = 3.6; N = 25.4 | 274 | 276 |
| 99 | 4-fluoroanilino | methylthio | C = 51.9; H = 3.4; N = 25.6 | 274 | 276 |
| 100 | 2-hydroxyanilino | methylthio | C = 52.5; H = 4.0; N = 25.8 | 272 | 274 |
| 101 | 3-hydroxyanilino | methylthio | C = 52.5; H = 4.0; N = 25.7 | 272 | 274 |
| 102 | 2-methoxyanilino | methylthio | C = 54.3; H = 4.4; N = 24.6 | 286 | 288 |
| 103 | 3-methoxyanilino | methylthio | C = 54.0; H = 4.4; N = 24.9 | 286 | 288 |
| 104 | 4-methoxyanilino | methylthio | C = 53.8; H = 4.3; N = 24.7 | 286 | 288 |

TABLE 5-continued

Compounds Prepared by the Method of Example 15

| | PURINE SUBSTITUENT | | CHN ANALYSES | MS ANALYSES-ZMD | |
|---|---|---|---|---|---|
| | R6 | R2 | [%] | [M − H]⁻ a) | [M + H]⁺ b) |
| 105 | 3,4-dimethoxyanilino | methylthio | C = 52.6; H = 4.7; N = 22.2 | 316 | 318 |
| 106 | 2,5-dimethoxyanilino | methylthio | C = 52.9; H = 4.8; N = 22.2 | 316 | 318 |
| 107 | 2-chloro-5-methoxyanilino | methylthio | C = 48.8; H = 4.7; N = 22.0 | 320 | 322 |
| 108 | 2-methoxy-3-chloroanilino | methylthio | C = 48.1; H = 5.3; N = 21.3 | 320 | 322 |

Example 16

2-Methyl-6-(3-methoxyanilino)purine

To a suspension of 2-methyl-6-chloropurine (1.69 g; 0.01 mol) and m-anisidine (1.23 g; 0.01 mol) in n-butanol (20 ml), triethylamine (3.5 ml; 0.025 mol) was added. The resulting thick suspension was stirred at 110° C. for 3 hours, when TLC showed the absence of starting material and the presence of desired product. The reaction mixture was then cooled to room temperature. The white precipitate was filtered off, rinsed with n-butanol (2×10 ml) and water (3×10 ml) and dried into constant weight. Yield: 1.92 g (75%). The crude product was purified as hydrochloride salt by the crystallization from 2.5 M methanolic hydrochloric acid. TLC (chloroform-methanol-NH₄OH; 4:1:0.05): one single spot, free of starting material. HPLC purity: 99+%.

TABLE 6

Compounds Prepared by the Method of Example 16

| | PURINE SUBSTITUENT | | CHN ANALYSES | MS ANALYSES-ZMD | |
|---|---|---|---|---|---|
| | R6 | R2 | [%] | [M − H]⁻ a) | [M + H]⁺ b) |
| 109 | anilino | methyl | C = 63.8; H = 4.9; N = 31.2 | 224 | 226 |
| 110 | 2-chloroanilino | methyl | C = 55.3; H = 3.7; N = 27.3 | 258 | 260 |
| 111 | 3-chloroanilino | methyl | C = 55.3; H = 3.8; N = 27.3 | 258 | 260 |
| 112 | 2-fluoroanilino | methyl | C = 59.0; H = 4.1; N = 29.0 | 242 | 244 |
| 113 | 3-fluoroanilino | methyl | C = 59.2; H = 4.2; N = 29.1 | 242 | 244 |
| 114 | 4-fluoroanilino | methyl | C = 59.1; H = 4.1; N = 29.0 | 242 | 244 |
| 115 | 2-hydroxyanilino | methyl | C = 60.0; H = 4.6; N = 29.2 | 240 | 242 |
| 116 | 3-hydroxyanilino | methyl | C = 59.9; H = 4.6; N = 29.1 | 240 | 242 |
| 117 | 2-methoxyanilino | methyl | C = 61.1; H = 5.2; N = 27.9 | 254 | 256 |
| 118 | 3-methoxyanilino | methyl | C = 60.8; H = 5.1; N = 27.5 | 254 | 256 |
| 119 | 4-methoxyanilino | methyl | C = 61.0; H = 5.1; N = 27.5 | 254 | 256 |
| 120 | 3,4-dimethoxyanilino | methyl | C = 58.5; H = 5.1; N = 24.9 | 284 | 286 |
| 121 | 2,5-dimethoxyanilino | methyl | C = 58.8; H = 5.1; N = 24.6 | 284 | 286 |
| 122 | 2-chloro-5-methoxyanilino | methyl | C = 53.7; H = 4.1; N = 24.3 | 288 | 290 |
| 123 | 2-methoxy-3-chloroanilino | methyl | C = 53.8; H = 4.2; N = 24.6 | 288 | 290 |

Example 17

2-Bromo-6-(methoxyanilino)purine

2-Bromo-6-(methoxyanilino)purine was prepared in a similar manner to example 5 by the reaction of 2-bromo-6-chloropurine and m-anisidine (molar ratio 1:1) in the presence of triethylamine (2.5 eq.) in n-propanol at 100° C. for 4 hours. After cooling to room temperature the resulting white precipitate was filtered off, washed with cold n-propanol and water and dried in desiccator into constant weight. Yield: 69% (as hydrobromide). Crude product was purified by crystallization from methanol and free base was obtained by treatment of hydrobromide with 10% aqueous ammonia. HPLC purity: 98+%.

TABLE 7

Compounds Prepared by the Method of Example 17

| | PURINE SUBSTITUENT | | CHN ANALYSES | MS ANALYSES-ZMD | |
|---|---|---|---|---|---|
| | R6 | R2 | [%] | $[M - H]^-$ a) | $[M + H]^+$ b) |
| 124 | Anilino | bromo | C = 45.4; H = 2.7; N = 24.3 | 289 | 291 |
| 125 | 2-chloroanilino | bromo | C = 40.5; H = 2.1; N = 21.7 | 323 | 325 |
| 126 | 3-chloroanilino | bromo | C = 40.5; H = 2.1; N = 21.6 | 323 | 325 |
| 127 | 2-fluoroanilino | bromo | C = 44.5; H = 2.1; N = 23.0 | 307 | 309 |
| 128 | 3-fluoroanilino | bromo | C = 44.7; H = 2.1; N = 22.9 | 307 | 309 |
| 129 | 3-methoxyanilino | bromo | C = 44.6; H = 3.2; N = 21.6 | 319 | 321 |
| 130 | 2-hydroxyanilino | bromo | C = 42:9; H = 2.6; N = 23.1 | 305 | 307 |
| 131 | 3-hydroxyanilino | bromo | C = 43.2; H = 4.6; N = 22.9 | 305 | 307 |

Example 18

2-Nitro-6-(3-methoxyphenyl)amino-9-Boc-purine

To a solution of 2-nitro-6-chloro-9-tetrahydropyranylpurine (3.00 g; 0.01 mol) in methanol (40 ml) at 0° C., a solution of m-anisidine (1.48 g; 0012 mol) and triethylamine (3.0 g=4.2 ml; 0.03 mol) in methanol (10 ml) was slowly added dropwise so that the temperature of the reaction mixture does not exceed +5° C. After addition of m-anisidine the reaction mixture was allowed to warm up to room temperature while stiffing. The course of the reaction was monitored by TLC—the absence of the spot of starting 2-nitro-6-chloro-9-tetrahydropyranylpurine shows the end of reaction. Methanol was evaporated on rotary vacuum evaporator and the semi solid residue was partitioned between water (50 ml) and ethyl acetate (50 ml). The aqueous layer was extracted with more ethyl acetate (50 ml). Combined organic layers were washed with water (20 ml), dried with anhydrous MgSO$_4$, and evaporated into dryness. The crude product was crystallized from ether:cyclohexane (1:1, v/v). Yield: 3.1 g (80%) of almost white crystalline product; purity (HPLC): 98%+.

Example 19

2-Nitro-6-(3-methoxyphenyl)aminopurine

2-Nitro-6-(3.methoxyphenyl)amino-9-Boc-purine (3.86 g; 0.01 mol) was dissolved in 50% trifluoroacetic acid (50 ml) at 0° C. The solution was stored in refrigerator overnight. Trifluoroacetic acid and water were evaporated on rotary vacuum evaporator and the crystalline residue was treated with cold 5% aqueous ammonia (100 ml). The crude product was collected by filtration and re-crystallized from 50% methanol. Yield: 1.97 g (69%) of yellowish crystalline product; purity (HPLC): 98%+.

TABLE 8

Compounds Prepared by the Method of Examples 18-19

| | PURINE SUBSTITUENT | | CHN ANALYSES | MS ANALYSES-ZMD | |
|---|---|---|---|---|---|
| | R6 | R2 | [%] | $[M - H]^-$ a) | $[M + H]^+$ b) |
| 124 | anilino | nitro | C = 55.1; H = 3.4; N = 35.1 | 239 | 241 |
| 125 | 2-chloroanilino | nitro | C = 47.9; H = 2.6; N = 30.9 | 273 | 275 |
| 126 | 3-chloroanilino | nitro | C = 48.0; H = 2.6; N = 30.7 | 273 | 275 |
| 127 | 2-fluoroanilino | nitro | C = 51.0; H = 2.6; N = 32.8 | 257 | 259 |
| 128 | 3-fluoroanilino | nitro | C = 51.1; H = 2.7; N = 32.8 | 257 | 259 |
| 129 | 3-methoxyanilino | nitro | C = 53.1; H = 3.6; N = 31.5 | 269 | 271 |
| 130 | 2-hydroxyanilino | nitro | C = 51.5; H = 3.1; N = 33.0 | 255 | 257 |
| 131 | 3-hydroxyanilino | nitro | C = 51.3; H = 2.9; N = 32.9 | 255 | 257 |

Example 20

Inhibition of Cytokinin Oxidase/Dehydrogenase Activity

IC$_{50}$ determinations were done using the assay in microtitre plate. Each well contained 100 μL of PMS/MTT [phenazine methosulfate/3-(4,5-dimethylthiazol-2-yl)-2,5-diphenyltetrazolium bromide] reaction mixture (final concentrations: 0.1 M $KH_2PO_4$, pH 7.4, 1 mM MTT, 0.2 mM PMS) containing the tested compound ($3\times10^{-7}$ M-$3\times10^{-4}$ M) and 30 μM $N^6$-isopentenyladenine (iP) as a substrate. 100 μL of cell-free growth medium of *S. cerevisiae* strain 23344c ura⁻ harbouring the plasmid pYES2-AtCKX2 was directly used as a source of AtCKX2. Plates were incubated in the dark for 30 mM at 37° C. and the enzymatic reaction was stopped by 25 μL of 35% acetic acid. The absorbance at 578 nm was measured using spectrophotometer Tecan. Absorbance of the sample without iP was subtracted.

The $IC_{50}$ value, the compound concentration that inhibits the enzyme activity to 50%, was calculated from the obtained dose response curves. The values shown in Table 9 are means of three replicates and the entire test was repeated at least twice. More potent compounds than thidiazuron have $IC_{50}$ values lower than thidiazuron.

TABLE 9

The effect of novel compounds on inhibition of recombinant AtCKX2

| No. | Tested compound R6 | R2 | IC50 (μmol · L⁻¹) |
|---|---|---|---|
|  | thidiazuron |  | 30 |
| 1 | anilino | chloro | 22.6 |
| 3 | 3-chloroanilino | chloro | 6.3 |
| 4 | 4-chloroanilino | chloro | 24.1 |
| 6 | 3-fluoroanilino | chloro | 12.2 |
| 9 | 3-hydroxyanilino | chloro | 3.5 |
| 12 | 3-methoxyanilino | chloro | 0.8 |
| 42 | 3-chloroanilino | fluoro | 15.3 |
| 43 | 4-chloroanilino | fluoro | 27 |
| 45 | 3-fluoroanilino | fluoro | 22.1 |
| 48 | 3-hydroxyanilino | fluoro | 11.8 |
| 51 | 3-methoxyanilino | fluoro | 0.4 |
| 66 | 3-chloroanilino | amino | 25.6 |
| 69 | 3-fluoroanilino | amino | 29.4 |
| 75 | 3-methoxyanilino | amino | 24.7 |
| 80 | 3-chloroanilino | thio | 28.4 |
| 83 | 3-fluoroanilino | thio | 22.6 |
| 88 | 3-methoxyanilino | thio | 28.3 |
| 111 | 3-chloroanilino | methyl | 15.7 |
| 113 | 3-fluoroanilino | methyl | 21.8 |
| 118 | 3-methoxyanilino | methyl | 9.4 |
| 126 | 3-chloroanilino | nitro | 5.8 |
| 128 | 3-fluoroanilino | nitro | 11.0 |
| 129 | 3-methoxyanilino | nitro | 0.6 |

Example 21

In vivo effect of 2-chloro-6-(3-methoxyanilino)aminopurine (compound 12)

Figure 2:
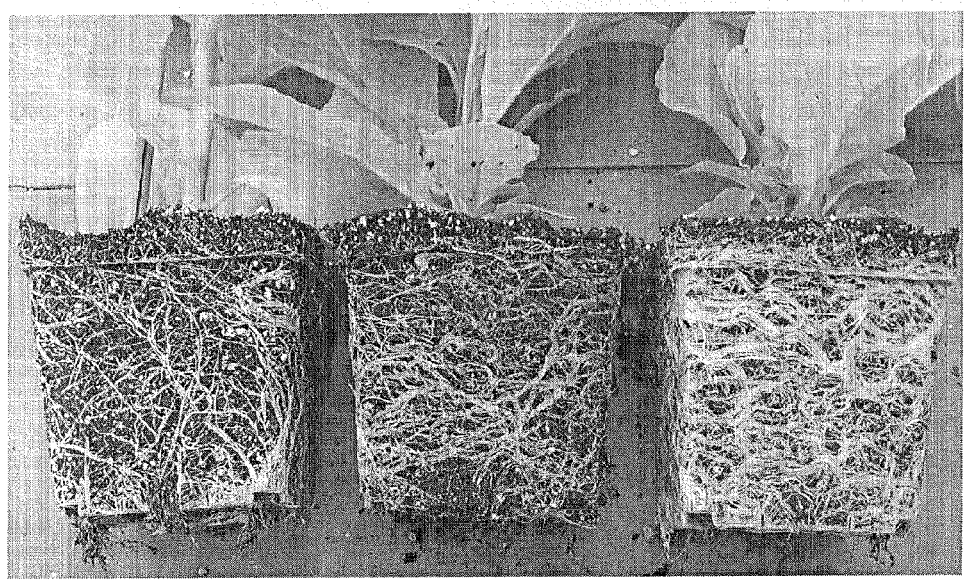
FIG. 2 documents the effect of foliar application of compound 12 on root enhancement of CKX overproducing tobaccos. − means not treated, + means treated.
Figure 3:
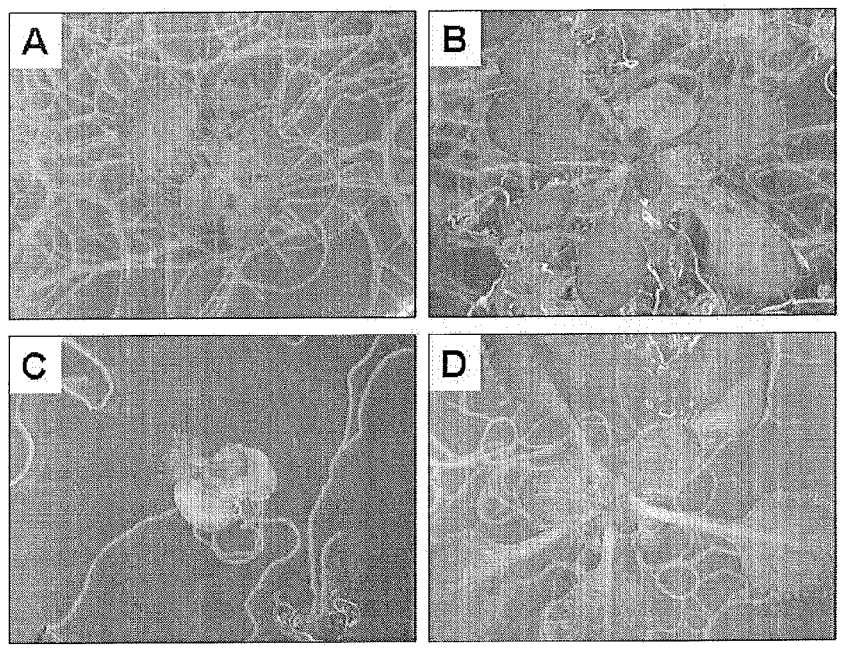
FIG. 3 shows comparison of effect of cytokinin and CKX inhibitor application on complementation of wild-type phenotype of AtCKX1 *Arabidopsis* seedlings. (A) AtCKX1, (B) AtCKX1 cultivated on 0.1 µM compound 12, (C) AtCKX1 cultivated on 0.1 µM BAP, (D) control plant with wild-type phenotype.

Transgenic 35S:AtCKX1 *Arabidopsis* and 35S:AtCKX1 and 35S:AtCKX2 tobacco seedlings grown in soil in the greenhouse were systematically treated with 10 μM of compound 12. Areal parts of the wild type and transgenic seedlings were sprayed every second day for 1 month with aqueous solution of compound 12 containing 0.01% Silwet L-77 wetting agent. FIG. 1 clearly shows that the application of CKX inhibitor 2-chloro-6-(3-methoxyanilino)aminopurine (compound 12) released the plants from growth inhibition caused by decreased cytokinin level and led to restauration of wild type phenotype. Interestingly, the foliar application of compound 12 led to the enhancement of the root system of the transgenic tobaccos (FIG. 2). To prove that the phenotype complementation effect is not general effect of exogenously applied cytokinin, but specific effect of CKX-inhibitor, CKX1 overproducing *Arabidopsis* seedlings were grown in vitro on MS medium containing 0.1 μM cytokinin BAP (FIG. 3C) or the same concentration of compound 12 (FIG. 3B). The reversion of WT phenotype appeared only when the compound 12 was present in the medium.

Figure 4:
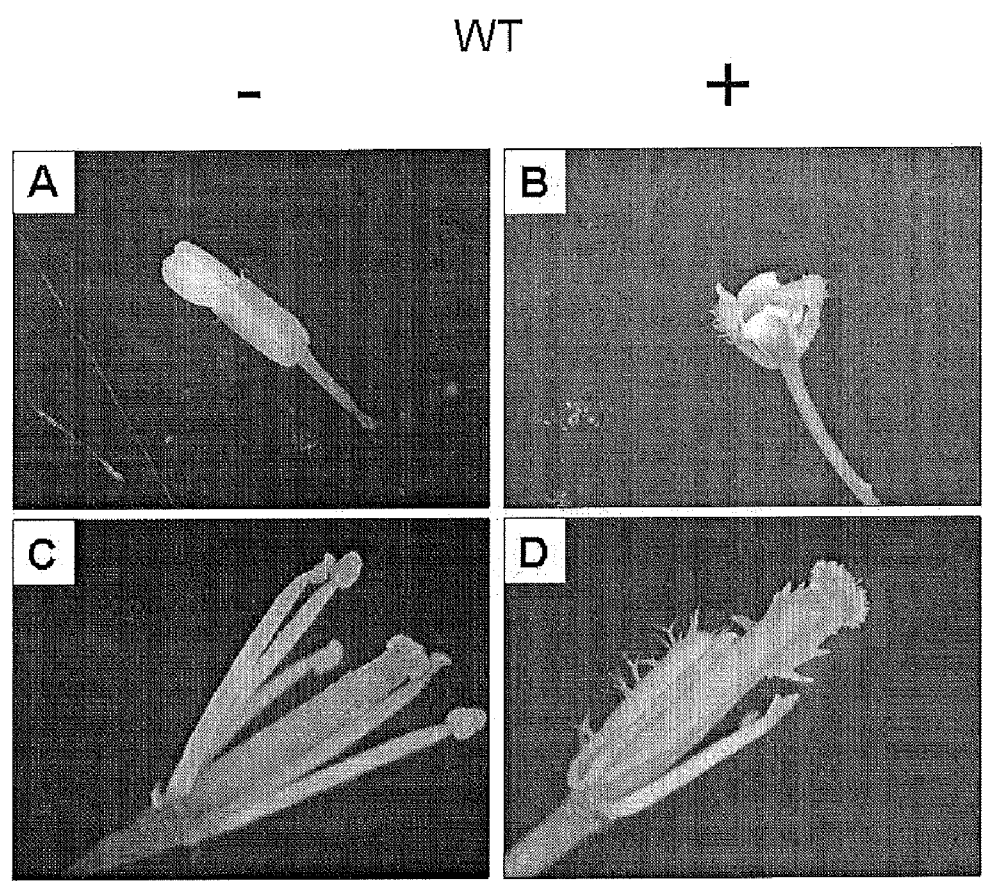
FIG. 4 illustrates the effect of compound 12 on flowering of *Arabidopsis* plants.

Prolonged treatment of WT *Arabidopsis* plants led to altered development of flowers and inhibition of fertilisation (FIG. 4). Flowers had aborted anthers and were sterile.

Example 22

Activation of Cytokinin Receptors

*Escherichia coli* strains KMI001 harbouring the plasmid pIN-III-AHK4 or pSTV28-AHK3 were grown overnight at 25° C. in M9 media enriched with 0.1% casamino acids to $OD_{600}$~1. The preculture was diluted 1:600 in 1 ml M9 medium containing 0.1% casamino acids and 1 μl stock solution of either the tested compound ($10^{-7}$ M-$5\times10^{-5}$ M) or solvent control (DMSO, ethanol, methanol) were added. The cultures were further grown at 25° C. in microtiter plate, 200 μl per well. Incubation times of 17 h and 28 h were found to be optimal for CRE1/AHK4 and AHK3, respectively. The cultures were centrifuged and 50 μl aliquots of the supernatant were transferred to microtiter plate containing 2 μl 150 mM 4-methyl umbelliferyl galactoside which was subsequently incubated for 1 h at 37° C. The reaction was stopped by adding 100 μl 0.2 M $Na_2CO_3$. Fluorescence was measured using a Fluoroscan Ascent (Labsystems, Finland) at the excitation and emission wavelengths of 365 and 460 nm, respectively. The $OD_{600}$ of the remaining culture was determined and β-galactosidase activity was calculated as nmol 4-methylumbelliferone×$OD_{600}^{-1}$×$h^{-1}$.

The $EC_{50}$ value, the compound concentration activating the receptor to 50%, was calculated from the obtained dose response curves. The values shown in Table 10 are means of three replicates and the entire test was repeated at least twice. The compounds which activate cytokinin receptors to much lower extent then trans-zeatin are useful as CKX inhibitors. New substituted 6-anilinopurines have much lower affinity for *A. thaliana* cytokinin receptors than trans-zeatin.

TABLE 10

The effect of novel compounds on activation of cytokinin receptors of *Arabidopsis thaliana* CRE1/AHK4 and AHK3.

| No. | Tested compound R6 | R2 | EC50 (μmol · L⁻¹) CRE1/AHK4 | AHK3 |
|---|---|---|---|---|
|  | trans-zeatin |  | 0.9 | 2.1 |
|  | benzylamino |  | 19.7 | 18.2 |
| 1 | anilino | chloro | n.a. | >50 |
| 3 | 3-chloroanilino | chloro | 7.5 | 20 |
| 7 | 4-fluoroanilino | chloro | n.a. | 50 |
| 8 | 2-hydroxyanilino | chloro | >50 | 31.7 |
| 9 | 3-hydroxyanilino | chloro | 37.1 | 2.8 |
| 12 | 3-methoxyanilino | chloro | 31.3 | 9.5 |
| 13 | 4-methoxyanilino | chloro | n.a. | 33.1 |
| 30 | 3,4-dimethylanilino | chloro | 33.3 | >50 |
| 40 | anilino | fluoro | 46.2 | 19 |
| 42 | 3-chloroanilino | fluoro | 21 | 31.6 |
| 43 | 4-chloroanilino | fluoro | 39.8 | 27 |
| 45 | 3-fluoroanilino | fluoro | >50 | 42.1 |
| 46 | 4-fluoroanilino | fluoro | n.a. | 22.5 |
| 47 | 2-hydroxyanilino | fluoro | >50 | 45.8 |
| 48 | 3-hydroxyanilino | fluoro | 49.6 | 15 |
| 49 | 4-hydroxyanilino | fluoro | 37.1 | >50 |
| 50 | 2-methoxyanilino | fluoro | >50 | 17.4 |

TABLE 10-continued

The effect of novel compounds on activation of cytokinin receptors of *Arabidopsis thaliana* CRE1/AHK4 and AHK3.

| No. | Tested compound R6 | R2 | EC50 ($\mu mol \cdot L^{-1}$) CRE1/AHK4 | AHK3 |
|---|---|---|---|---|
| 51 | 3-methoxyanilino | fluoro | 43 | 22.7 |
| 52 | 4-methoxyanilino | fluoro | n.a. | 18.9 |
| 64 | anilino | amino | n.a. | 25.3 |
| 66 | 3-chloroanilino | amino | n.a. | 43 |
| 67 | 4-chloroanilino | amino | n.a. | 8.1 |
| 69 | 3-fluoroanilino | amino | n.a. | >50 |
| 70 | 4-fluoroanilino | amino | n.a. | 19.5 |
| 71 | 2-hydroxyanilino | amino | >50 | >50 |
| 72 | 3-hydroxyanilino | amino | >50 | 7.7 |
| 73 | 4-hydroxyanilino | amino | >50 | >50 |
| 74 | 2-methoxyanilino | amino | n.a. | 29 |
| 75 | 3-methoxyanilino | amino | n.a. | 20.4 |
| 76 | 4-methoxyanilino | amino | n.a. | 26.3 |
| 80 | 3-chloroanilino | thio | n.a. | 42 |
| 81 | 4-chloroanilino | thio | n.a. | 10.2 |
| 83 | 3-fluoroanilino | thio | n.a. | >50 |
| 88 | 3-methoxyanilino | thio | n.a. | 31.7 |
| 96 | 3-chloroanilino | methylthio | 41 | 29 |
| 98 | 3-fluoroanilino | methylthio | 49 | 32 |
| 111 | 3-chloroanilino | methyl | n.a. | >50 |
| 113 | 3-fluoroanilino | methyl | n.a. | n.a. |
| 118 | 3-methoxyanilino | methyl | n.a. | >50 | n.a. means no activation

Example 23

Stimulatory Effect of Novel Compounds on Plant Cell Division

The stimulatory effect of the newly prepared derivatives was tested in the calus biotest using cytokinin-dependent tobacco callus. Cytokinin-dependent tobacco callus *Nicotiana tabacum* L. cv. Wisconsin 38 was maintained at 25° C. in darkness on modified Murashige-Skoog medium, containing per 1 liter: 4 µmol of nicotinic acid, 2.4 µmol of pyridoxine hydrochloride, 1.2 µmol of thiamine, 26.6 µmol of glycine, 1.37 µmol of glutamine, 1.8 µmol of myo-inositol, 30 g of sucrose, 8 g of agar, 5.37 µmol of NAA and 0.5 µmol of 6-benzylaminopurine. Subcultivation was carried out every three weeks. Fourteen days before the bioassay, the callus tissue was transferred to the media without 6-benzylaminopurine. The biological activity was determined from the increase of the fresh callus weight after four weeks of cultivation. Five replicates were prepared for each concentration of the compound tested and the entire test was repeated twice. Kinetin, which is known to be highly active cytokinin, was used in each experiment as a control. The compounds to be tested were dissolved in dimethylsulfoxide (DMSO) and the solution brought up to $10^{-3}$ M with distilled water. This stock solution was further diluted with the respective media used for the biotest to a concentration ranging from $10^{-8}$ M to $10^{-4}$ M. The final concentration of DMSO did not exceed 0.2% and therefore did not affect the biological activity in the assay system used.

From the obtained data, the concentration with the highest activity was selected for each compound tested. Relative activity of the compound at this concentration was calculated (Table 11). The activity obtained for $10^{-5}$ M of the control substance kinetin (K) was postulated as 100%.

The results in Table 11 show that the substitution in position 2 and 6 of the purine ring led to an increase of the cytokinin activity in the callus bioassay in comparison to the classical cytokinin kinetin (K).

TABLE 11

The effect of novel compounds on the growth of cytokinin-dependent tobacco callus *Nicotiana tabacum* L. cv. Wisconsins 38

| No. | Tested compound R6 | R2 | concentration with highest activity ($mol \cdot l^{-1}$) | activity (%) [$10^{-5}$ $mol \cdot l^{-1}$ K = 100%] |
|---|---|---|---|---|
| C | furfurylamino | H | $10^{-5}$ | 100 |
| 3 | 3-chloroanilino | Chloro | $10^{-5}$ | 110 (±6) |
| 4 | 4-chloroanilino | Chloro | $10^{-5}$ | 102 (±8) |
| 6 | 3-fluoroanilino | Chloro | $10^{-5}$ | 119.7 (±8) |
| 7 | 4-fluoroanilino | Chloro | $10^{-5}$ | 112 (±12) |
| 9 | 3-hydroxyanilino | Chloro | $10^{-5}$ | 116.2 (±13) |
| 11 | 2-methoxyanilino | Chloro | $10^{-5}$ | 109 (±5) |
| 12 | 3-methoxyanilino | Chloro | $10^{-5}$ | 122 (±3) |
| 40 | anilino | Fluoro | $10^{-5}$ | 108.1 (±4) |
| 42 | 3-chloroanilino | Fluoro | $10^{-5}$ | 121 (±8) |
| 43 | 4-chloroanilino | Fluoro | $10^{-5}$ | 130 (±6) |
| 45 | 3-fluoroanilino | Fluoro | $10^{-5}$ | 127.9 (±8) |
| 46 | 4-fluoroanilino | Fluoro | $10^{-5}$ | 110.7 (±5) |
| 48 | 3-hydroxyanilino | Fluoro | $10^{-5}$ | 104.2 (±3) |
| 49 | 4-hydroxyanilino | Fluoro | $10^{-5}$ | 106 (±3) |
| 50 | 2-methoxyanilino | Fluoro | $10^{-5}$ | 117.6 (±9) |
| 51 | 3-methoxyanilino | Fluoro | $10^{-5}$ | 120.5 (±13) |
| 52 | 4-methoxyanilino | Fluoro | $10^{-5}$ | 105 (±7) |
| 80 | 3-chloroanilino | Thio | $10^{-5}$ | 126 (±5) |
| 81 | 4-chloroanilino | Thio | $10^{-5}$ | 115.7 (±4) |
| 83 | 3-fluoroanilino | Thio | $10^{-5}$ | 102.5 (±10) |
| 88 | 3-methoxyanilino | Thio | $10^{-5}$ | 103.4 (±12) |
| 96 | 3-chloroanilino | Methylthio | $10^{-5}$ | 121.2 (±18) |
| 98 | 3-fluoroanilino | Methylthio | $10^{-5}$ | 130.3 (±17) |
| 103 | 3-methoxyanilino | Methylthio | $10^{-5}$ | 142.8 (±21) |
| 111 | 3-chloroanilino | Methyl | $10^{-5}$ | 128.3 (±6) |
| 113 | 3-fluoroanilino | Methyl | $10^{-5}$ | 125.3 (±7) |
| 118 | 3-methoxyanilino | Methyl | $10^{-5}$ | 105.7 (±5) |

Example 24

Testing of Novel Cytokinins in *Amaranthus* Bioassay

The standard *Amaranthus* bioassay was performed with the following modifications. The seeds of *Amaranthus caudatus* var. *atropurpurea* were surface-sterilised in 10% (w/v) N-chlorobenzenesulfonamide for 10 min and washed 5 times with deionized water. They were placed in 15 cm Petri dishes containing paper tissues saturated with deionized water. After 72 h of cultivation at 25° C. in darkness, the roots of the seedlings were cut off. The explants, consisting of two cotyledons and hypocotyls, were placed in 5 cm Petri dishes onto two layers of filtration paper soaked with 1 ml of the incubation medium containing 10 µmol of $Na_2HPO_4$—$KH_2PO_4$, pH 6.8, 5 µmol of tyrosine and the compound to be tested. There were 20 explants per dish. The procedure was carried out under green safe light in a darkroom. After 48 h of incubation at 25° C. in darkness, betacyanin was extracted by freezing the explants in 4 ml 3.33 µM acetic acid. The concentration of betacyanin was determined from the absorbances at 537 nm and 620 nm as follows: $\Delta A = A_{537nm} - A_{620nm}$. The values $\Delta A$ were plotted against the concentration tested, are means of five replicates and the entire test was repeated at least twice. Kinetin, which is known to be highly active cytokinin, was used in each experiment as a control. The compounds to be tested were dissolved in dimethylsulfoxide (DMSO) and the solution brought up to $10^{-3}$ M with distilled water. This stock solution was further diluted with the respective media used for the biotest to a concentration ranging from $10^{-8}$ M to $10^{-4}$ M. The final concentration of DMSO did not exceed 0.2% and therefore did not affect the biological activity in the assay system used.

From the obtained data, the concentration with the highest activity was selected for each compound tested. Relative activity of the compound at this concentration was calculated (Tab. 12). The activity obtained for $10^{-5}$ M kinetin (K) was postulated as 100%.

The results show that the substitution in the positions 2 and 6 of the purine skeleton led to an increase of betacyanin (purple colour) content in *Amaranthus caudatus* cotyledon/hypocotyl explants in comparison to kinetin (K).

TABLE 12

The effect of novel compounds on the betacyanin content in *Amaranthus caudatus* cotyledon/hypocotyl explants

| No. | Tested compound R6 | R2 | Concentration with highest activity (mol·l$^{-1}$) | Activity (%) [$10^{-5}$ mol·l$^{-1}$ K = 100%] |
|---|---|---|---|---|
| C | furfurylamino | H | $10^{-5}$ | 100 |
| 3 | 3-chloroanilino | chloro | $10^{-5}$ | 166 (±4) |
| 4 | 4-chloroanilino | chloro | $10^{-5}$ | 107 (±8) |
| 6 | 3-fluoroanilino | chloro | $10^{-5}$ | 120 (±15) |
| 7 | 4-fluoroanilino | chloro | $10^{-5}$ | 104 (±4) |
| 9 | 3-hydroxyanilino | chloro | $10^{-5}$ | 115.4 (±18) |
| 11 | 2-methoxyanilino | chloro | $10^{-5}$ | 110.3 (±15) |
| 12 | 3-methoxyanilino | chloro | $10^{-5}$ | 132.3 (±14) |
| 40 | anilino | fluoro | $10^{-5}$ | 107 (±5) |
| 42 | 3-chloroanilino | fluoro | $10^{-5}$ | 121 (±6) |
| 43 | 4-chloroanilino | fluoro | $10^{-5}$ | 102.6 (±1) |
| 45 | 3-fluoroanilino | fluoro | $10^{-5}$ | 105.1 (±13) |
| 46 | 4-fluoroanilino | fluoro | $10^{-5}$ | 109 (±8) |
| 48 | 3-hydroxyanilino | fluoro | $10^{-5}$ | 100.3 (±10) |
| 50 | 2-methoxyanilino | fluoro | $10^{-5}$ | 105.2 (±9) |
| 51 | 3-methoxyanilino | fluoro | $10^{-5}$ | 117.2 (±11) |
| 64 | anilino | amino | $10^{-5}$ | 125.2 (±14) |
| 66 | 3-chloroanilino | amino | $10^{-5}$ | 122 (±5) |
| 67 | 4-chloroanilino | amino | $10^{-5}$ | 141.7 (±6) |
| 69 | 3-fluoroanilino | amino | $10^{-5}$ | 113.2 (±10) |
| 70 | 4-fluoroanilino | amino | $10^{-5}$ | 136 (±7) |
| 72 | 3-hydroxyanilino | amino | $10^{-5}$ | 119.8 (±15) |
| 74 | 2-methoxyanilino | amino | $10^{-5}$ | 108 (±13) |
| 75 | 3-methoxyanilino | amino | $10^{-5}$ | 123.6 (±19) |
| 80 | 3-chloroanilino | thio | $10^{-5}$ | 106 (±4) |
| 81 | 4-chloroanilino | thio | $10^{-5}$ | 122.9 (±5) |
| 83 | 3-fluoroanilino | thio | $10^{-5}$ | 133.5 (±11) |
| 88 | 3-methoxyanilino | thio | $10^{-5}$ | 113.4 (±15) |
| 96 | 3-chloroanilino | methylthio | $10^{-5}$ | 145.8 (±23) |
| 98 | 3-fluoroanilino | methylthio | $10^{-5}$ | 142.5 (±15) |
| 103 | 3-methoxyanilino | methylthio | $10^{-5}$ | 156.4 (±18) |
| 11 | 3-chloroanilino | methyl | $10^{-5}$ | 121.7 (±5) |
| 113 | 3-fluoroanilino | methyl | $10^{-5}$ | 120.2 (±6) |
| 118 | 3-methoxyanilino | methyl | $10^{-5}$ | 144.2 (±8) |

Example 25

In Vitro Cytotoxic Activity of Novel Compounds

Absence of toxic effects against mammalian (especially human) cell lines in a wide concentration range is one of the requirements on compounds intended for use in agriculture and medicine. Because toxic compounds negatively influence metabolic processes in cells, many standard cytotoxicity assays are based on measurement of metabolisation rate of various artificial substrates. Resulting product is then quantified e.g. by means of spectrometry. The assays can be easily modified for use in 96-well plates. For evaluation of cytotoxic effect of compounds of this invention, a microtiter assay based on quantification of metabolisation of Calcein AM was used. The assay is widely used in drug screening programs and in chemosensitivity testing. In live cells, Calcein AM is enzymatically hydrolysed and accumulation of resulting calcein is manifested by green fluorescence.

Following human cell lines were used for routine screening of the compounds: T-lymphoblastic leukemia cell line CEM, promyelocytic leukemia cell line HL-60, erytroid leukemia cell line K-562, breast carcinoma cell line MCF-7, osteosarcoma cell line HOS and melanoma cell line G-361. Mouse cell lines B16-F10 (melanoma) and NIH-3T3 (fibroblasts) were used as well. The cells were maintained in Nunc/Corning 80 cm$^2$ plastic tissue culture flasks and cultured in cell culture medium (DMEM with 5 g/l glucose, 2 mM glutamine, 100 U/ml penicillin, 100 μg/ml streptomycin, 10% fetal calf serum and sodium bicarbonate).

The cell suspensions were prepared and diluted according to the particular cell type and the expected target cell density (2.500-30.000 cells per well based on cell growth characteristics) and pippetted (80 μl) into 96-well plates. Inoculates were allowed a pre-incubation period of 24 hours at 37° C. and 5% $CO_2$ for stabilisation. Tested compound was added in total volume of 20 μl of water at time zero. Usually, test compound was evaluated at six 3-fold dilutions. In routine testing, the highest concentration tested was 166.6 μM. All drug concentrations were tested in triplicates. Incubations of cells with the test compounds lasted for 72 hours at 37° C., in 5% $CO_2$ atmosphere and 100% humidity. At the end of incubation period Calcein AM in PBS was added into final concentration of 1 μg/ml. After another 1 hour of incubation fluorescence (FD) was measured with the Labsystem FIA Reader Fluoroscan Ascent (UK). Growth inhibition (GI) was estimated using the following equitation: GI=(mean $FD_{drug\ exposed\ wells}$−mean $FD_{blank}$)/(mean $FD_{control\ wells}$−mean $FD_{blank}$)×100%. The $GI_{50}$ value, the drug concentration causing 50% reduction of Calcein AM conversion, was calculated from the obtained dose response curves.

The cytotoxicity of the novel compounds was tested on a panel of mammalian cell lines of different histogenetic and species origin (Table 14). We show herein that the compounds of this invention don't have a significant toxic effect on the used mammalian cell lines. Interestingly, "classical cytokinins" represented by 6-substituted purines kinetin, isopentenyladenine, benzyl adenine, meta-topolin and ortho-topolin (which are known in the prior art) are in several cases more toxic than the novel compounds of this invention. Thus the novel compounds might be more suitable for agricultural and medicinal applications than "classical cytokinins".

TABLE 14

Cytotoxicity of novel compounds for different mammalian cell lines

| | Cell line tested/GI$_{50}$ (μmol/L) | | | | | | | |
|---|---|---|---|---|---|---|---|---|
| Compound | HOS | K-562 | MCF7 | B16-F0 | NIH-3T3 | G-361 | CEM | HL60 |
| Kinetin | >166.7 | 164.1 | >166.7 | | >166.7 | | 155.1 | |
| Isopentenyladenine | >166.7 | 146.9 | >166.7 | | >166.7 | | 92.2 | >166.7 |

TABLE 14-continued

Cytotoxicity of novel compounds for different mammalian cell lines

| Compound | \multicolumn{8}{c}{Cell line tested/GI$_{50}$ (μmol/L)} |
| --- | --- | --- | --- | --- | --- | --- | --- | --- |
|  | HOS | K-562 | MCF7 | B16-F0 | NIH-3T3 | G-361 | CEM | HL60 |
| Benzyladenine | >166.7 | 138.9 | 166.1 |  | >166.7 |  | >166.7 | >166.7 |
| trans-zeatin |  | >166.7 |  |  | >166.7 |  | >166.7 | >166.7 |
| meta-topolin | >166.7 | 128.4 | >166.7 | 90.6 | >166.7 | >166.7 | 90.1 | 79.2 |
| ortho-topolin | >166.7 | >166.7 | >166.7 | 150 | >166.7 | 103.4 | 69.2 | 78 |
| adenine |  | >166.7 | >166.7 |  | >166.7 |  | >166.7 | >166.7 |
| 1 | >166.7 |  | >166.7 |  | >166.7 |  | >166.7 |  |
| 3 | >166.7 |  | >166.7 |  | >166.7 |  | >166.7 |  |
| 4 | >166.7 | >166.7 | >166.7 |  | >166.7 |  | >166.7 |  |
| 6 | >166.7 | >166.7 | >166.7 |  | >166.7 |  |  |  |
| 9 | >166.7 |  | >166.7 |  | >166.7 |  |  |  |
| 12 | >166.7 |  | >166.7 |  | >166.7 |  |  |  |
| 40 | >166.7 |  | >166.7 |  | >166.7 |  | >166.7 |  |
| 42 | >166.7 |  | >166.7 |  | >166.7 |  | >166.7 |  |
| 48 | >166.7 | >166.7 | >166.7 |  | >166.7 |  |  |  |
| 51 | >166.7 |  | >166.7 |  | >166.7 |  |  |  |
| 64 | >166.7 |  | >166.7 |  | >166.7 |  |  |  |
| 66 | >166.7 |  | >166.7 |  | >166.7 |  |  |  |
| 72 | >166.7 |  | >166.7 |  | >166.7 |  |  |  |
| 73 | >166.7 |  | >166.7 |  | >166.7 |  |  |  |
| 78 | >166.7 |  | >166.7 |  | >166.7 |  |  |  |
| 83 | >166.7 |  | >166.7 |  | >166.7 |  |  |  |
| 87 | >166.7 |  | >166.7 |  | >166.7 |  |  |  |
| 94 | >166.7 |  | >166.7 |  | >166.7 |  |  |  |
| 101 | >166.7 |  | >166.7 |  | >166.7 |  |  |  |
| 103 | >166.7 |  | >166.7 |  | >166.7 |  |  |  |
| 116 | >166.7 |  | >166.7 |  | >166.7 |  |  |  |
| 131 | >166.7 |  | >166.7 |  | >166.7 |  |  |  |

Example 26

Anti-Aging Activity in Human Fibroblasts

In this example, effects of the compounds of this invention on the activity of a senescence biomarker senescence-associated β-galactosidase was studied. Human diploid fibroblasts HCA of various passage levels were used for this purpose. The tested compounds were added to the medium at each passage. After the incubation period, cells were washed with PBS and fixed with 2% formaldehyde and 0.2% glutaraldehyde in PBS. After another wash with PBS, they were incubated with the staining solution comprising potassium ferricyanide (5 mM), potassium ferrocyanide (5 mM), MgCl$_2$ (2 mM), X-gal (5-bromo-4-chloro-3-indolyl-β-D-galactopyranoside) (1 mg/ml), in citric/phosphate buffer (pH 6.0) at 37° C. (without CO$_2$) for at least 1 hour. Following the incubation period, the numbers of cells expressing senescence-associated β-galactosidase (blue cells) were counted using light microscope.

TABLE 15

The effect of the new compounds on number of senescent cells in human fibroblast cell culture

|  | Senescent Cells (%) | | |
| --- | --- | --- | --- |
| Compound | HCA passage 25 | HCA passage 50 | HCA passage 80 |
| Kinetin | 3 | 5 | 38 |
| 2-chloro-6-(4-hydroxyanilino)purine | 4 | 6 | 22 |
| 2-chloro-6-(3-methoxyanilino)purine | 5 | 5 | 24 |
| 2-chloro-6-(4-methoxyanilino)purine | 4 | 3 | 26 |
| 2-chloro-6-(3-methoxy-4-hydroxyanilino)purine | 4 | 6 | 25 |
| 2-amino-(4-hydroanilino)purine | 3 | 4 | 21 |

TABLE 15-continued

The effect of the new compounds on number of senescent cells in human fibroblast cell culture

|  | Senescent Cells (%) | | |
| --- | --- | --- | --- |
| Compound | HCA passage 25 | HCA passage 50 | HCA passage 80 |
| 2-methylthio-6-(4-hydroxyanilino)purine | 4 | 6 | 34 |
| 2-fluoro-6-(4-hydroxyanilino)purine | 3 | 4 | 18 |
| 2-fluoro-6-(3-methoxyanilino)purine | 3 | 5 | 29 |
| 2-amino-6-(3-methoxyanilino)purine | 4 | 4 | 22 |
| 2-chloro-6-(3-methoxy-4-hydroxyanilino)purine | 4 | 6 | 31 |
| 2-amino-(4-hydroxyanilino)purine | 4 | 4 | 18 |

The substituted 6-anilinopurine derivatives were generally more effective than kinetin in retaining lower numbers of senescent cells after 80 passages.

Example 27

Anti-Inflammatory Activity of New Substituted 6-Anilinopurines

Anti-inflammatory activity of several of the substituted 6-anilinopurine derivatives of this invention was determined; kinetin was also evaluated as a control. Rat C6 glioma (ATCC No. CCL107) was cultivated in monolayer in serum-free chemically defined medium containing Ham's F10/minimal essential medium (1:1 v/v), 2 mM L-glutamine, 1% (v/v) minimal essential medium vitamins (100×), 1% (v/v) minimal essential medium nonessential amino acids (100×), 100 U/ml penicillin, 100 mg/ml streptomycin, and 30 nM sodium selenite. Incubation was performed at 37° C. in a 100% humidified atmosphere. The assays were performed in the logarithmic growth phase at a density of $2.5 \times 10^5$ cells/cm². Intracellular cAMP synthesis was induced by addition of 5 mM (−)-isoproterenol; various amounts of test compounds were added at the same time as the (−)-isoproterenol. After 30 min incubation, the cellular amount of cAMP was determined using ELISA (cAMP-enzyme immunoassay kit from Amersham). The $I_{50}$ values were determined from the dose-response curve in duplicate. The following results were obtained:

|  | Anti-inflammatory Activity | |
| --- | --- | --- |
| Compound | $I_{50}$ (µM) | Effect |
| Kinetin (6-furfurylaminopurine) | 0 | Not active |
| 2-chloro-6-(2-hydroxyanilino)purine | 25 | Inhibition |
| 2-chloro-6-(4-hydroxyanilino)purine | 13 | Inhibition |
| 2-chloro-6-(3-methoxybenzylamino)purine | 7 | Inhibition |
| 2-chloro-6-(3,5-dimethoxybenzylamino)purine | 11 | Inhibition |

The substituted 6-anilinopurine derivatives demonstrated anti-inflammatory activity. Kinetin was inactive in the test protocol.

Example 28

Effect of the Novel Compounds on Adherence of Fibroblasts

Figure 5:
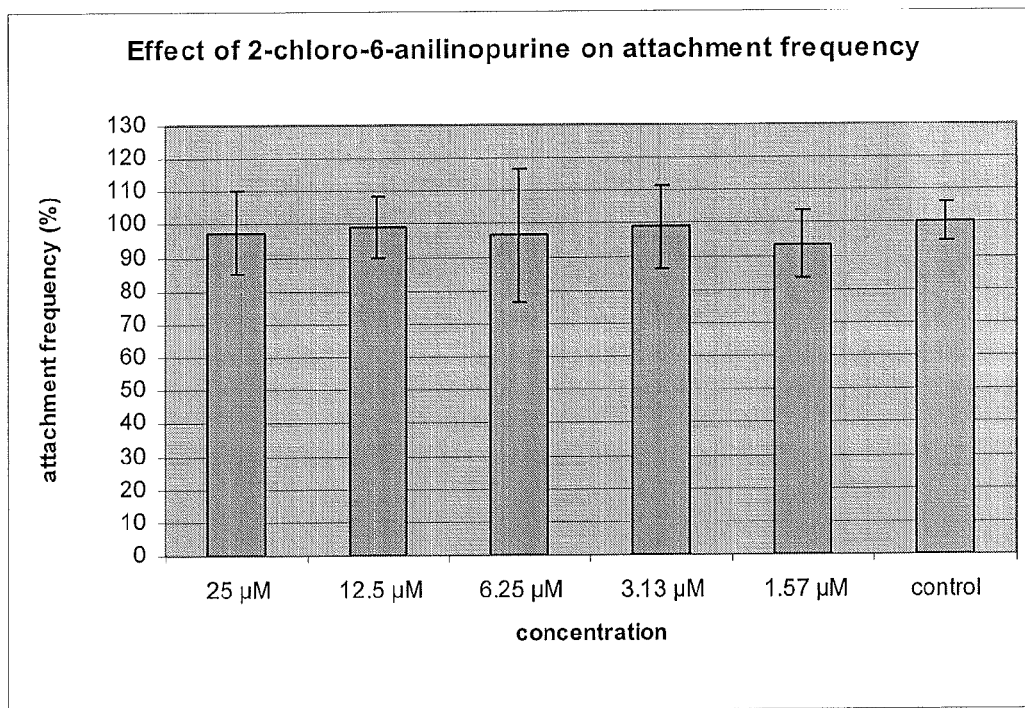
FIG. 5 shows the effect of 2-chloro-6-anilinopurine on attachment frequency of human fibroblasts. Values are shown relative to control.

Attachment frequency test is one of the methods for evaluation of acute toxicity of compounds against adherent cells. The tested compound is added into the medium with a defined number of trypsinised cells and after certain time the number of attached cells is counted. Human diploid fibroblasts BJ (passage 19) and standard cultivation medium (DMEM with 5 g/l glucose, 2 mM glutamin, 100 U/ml penicillin, 100 µg/ml streptomycin and 10% fetal calf serum) were used. The attached cells were counted after 6 hours. The experiment was done in three repetitions. The results are shown in FIG. 5. Attachment percentage was not significantly influenced by 2-chloro-6-anilinopurine in concentration range of 0-25 µM. Thus the compound doesn't show acute toxicity against fibroblasts.

Example 29

Evaluation of Viability of Human Diploid Fibroblast In Vitro by MTT Assay

Figure 6:
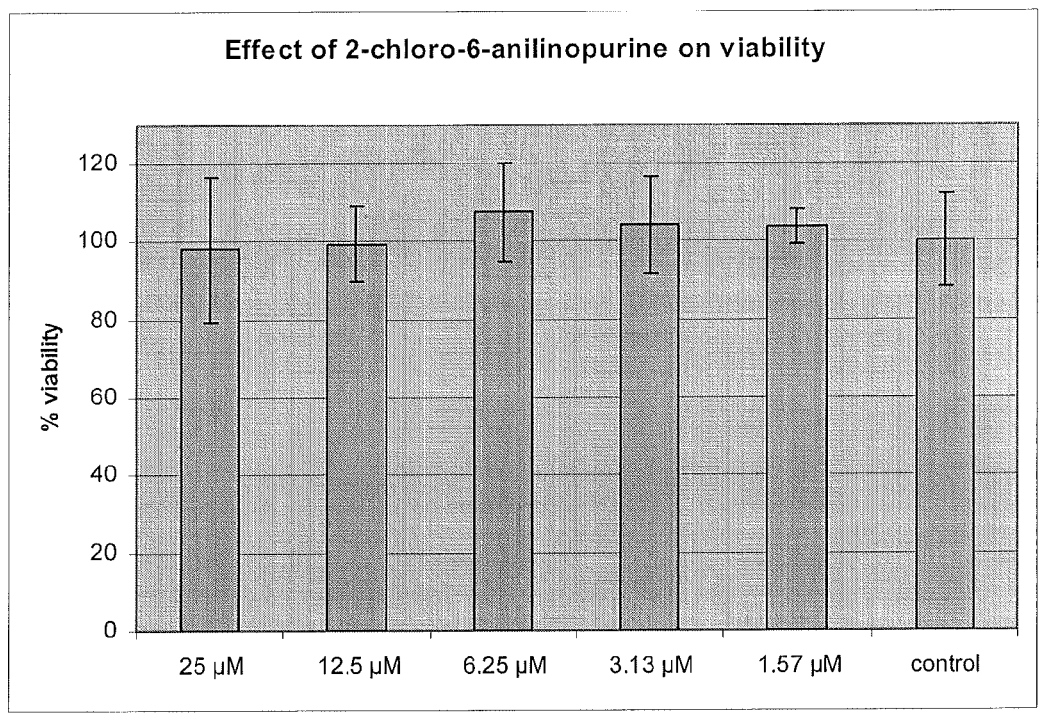
FIG. 6 illustrates the effect of 2-chloro-6-anilinopurine on viability of cells after 3 days. Values are shown relative to control.

MTT is a standard colorimetric assay for measurement of proliferation and survival of the cells. Yellow MTT is reduced into violet formazan in metabolically active cells. The amount of the resulting formazan is measured by spectrophotometry. Human diploid fibroblasts BJ (passage 19) were seeded in 96-well plate (5.000 cells per well). After 6 hours, the cultivation medium (DMEM containing 5 g/l glucose, 2 mM glutamine, 100 U/ml penicillin, 100 µg/ml streptomycin and 10% fetal calf serum) was removed and fresh medium containing a test compound in concentrations 0-25 µM was added. Each concentration was tested in 5 replicates. MTT was added to the cells after 72 hours into final concentration of 0.5 mg/ml. Incubation time was 3 hours. FIG. 6 shows the results for 2-chloro-6-anilinopurine. From the results it follows that this compound is not toxic for human diploid fibroblasts.

Example 30

In Vitro Toxicity in Human Diploid Fibroblasts by Evaluation of Growth Curve

Figure 7:
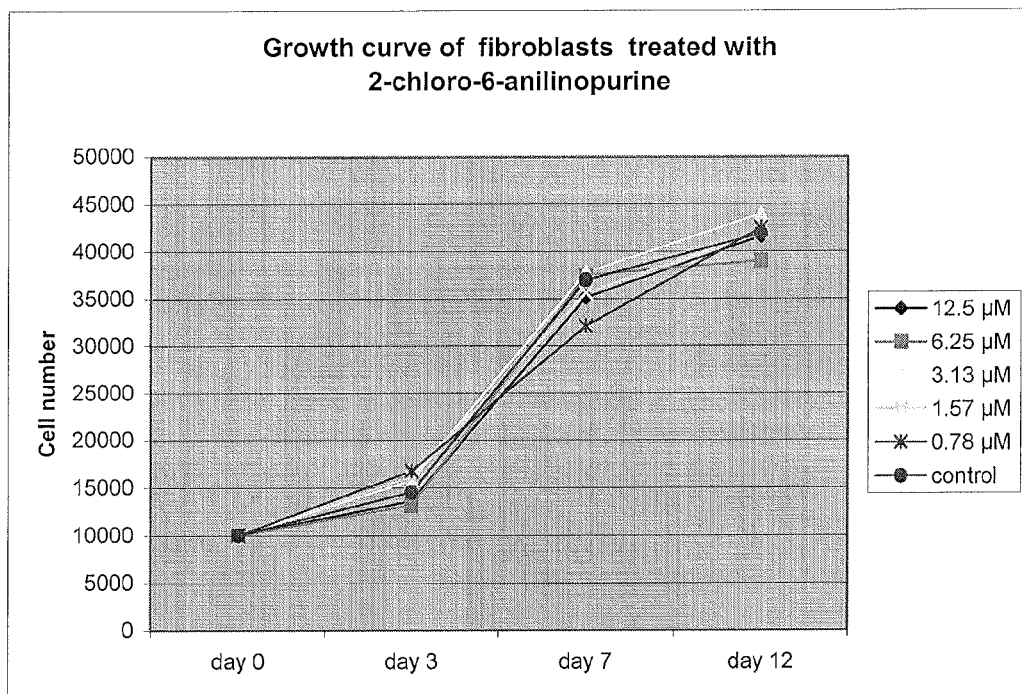
FIG. 7 shows growth curve of human diploid fibroblasts BJ treated with 2-chloro-6-anilinopurine.

Human diploid fibroblasts SNF25 (passage 27) were seeded in 24-well plate (10.000 cells/well). The cultivation medium (DMEM containing 5 g/l glucose, 2 mM glutamin, 100 U/ml penicillin, 100 µg/ml streptomycin and 10% fetal calf serum) was removed and replaced with the cultivation medium containing the tested compound in concentration range of 0-12.5 µM. Each concentration was tested in triplicate. The cell number was counted during next 12 days. FIG. 7 shows that the tested compound 2-chloro-6-anilinopurine was not toxic against human diploid fibroblasts in the concentration range and the time interval tested.

Example 31

Effect on Senescent Human Diploid Fibroblasts

Figure 8:
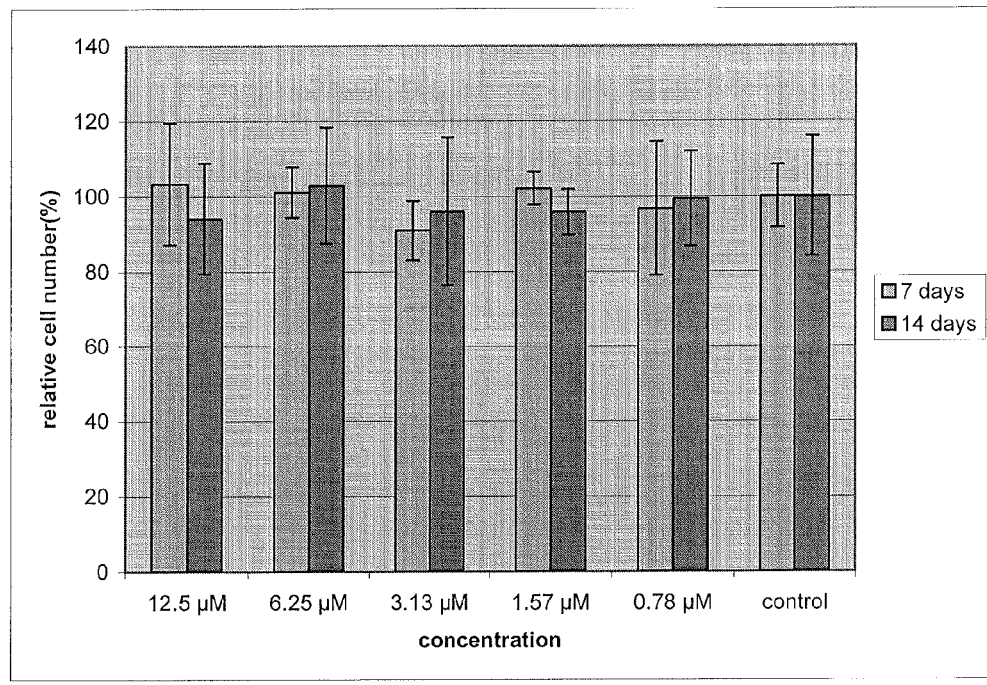
FIG. 8 shows cell number after treatment with 2-chloro-6-anilinopurine after 7 and 14 days. Values are shown relative to control.
Figure 9:
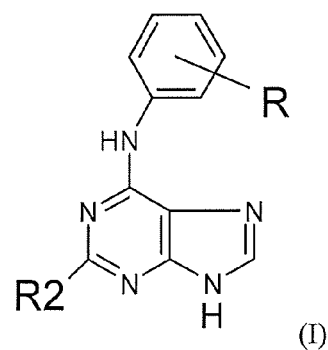
FIG. 9 shows the general formula I.

Senescent human diploid fibroblasts SNF25 (passage 53) were seeded in 24-well plate (10.000 cells/well). The cultivation medium (DMEM containing 5 g/l glucose, 2 mM glutamin, 100 U/ml penicillin, 100 mg/ml streptomycin and 10% fetal calf serum) was removed and replaced with the cultivation medium containing test compound in concentration range of 0-12.5 µM. Each concentration was tested in triplicate. The cell numbers were determined on days 7 and 14. FIG. 8 shows that 2-chloro-6-anilinopurine in the concentrations tested does not exert significant negative effect on cell survival in the time interval followed.

Example 32

Ames Test

Amest test was used in order to exclude mutagenic effect of 2-chloro-6-(4-hydroxyanilino)purine. Histidin auxotrophs of *Salmonella typhimurium* TA98 and TA100 were used as indicator strains and the test was carried out according to standard protocols (Ames et al., Mutation Research, 31, 347-364 (1975); Maron et al., Mutation Research, 113, 173-215 (1983)). Tested concentrations were as follows: 2.5, 5.0, 15, 50, 500, 1500, a 5000 µg/plate. The compound was not mutagenic even in the concentrations exceeding its solubility limit in the culture medium.

Example 33

Preparations

The growth regulatory preparations usually contain from 0.1 to 99% (w/w), preferably 0.1 to 95% (w/w), of active ingredient mixture comprising a compound of formula I, from 1 to 99.9% (w/w) of a solid or liquid adjuvant, and from 0.1 to 25% (w/w) of a surfactant. Whereas commercial products are usually formulated as concentrates, the end user will normally employ dilute formulations. The preparations may also comprise further ingredients, such as stabilisers, e.g. vegetable oils or epoxidised vegetable oils (epoxidised coconut oil 0;1, rapeseed oil or soybean oil), antifoams, e.g. silicone oil, preservatives, viscosity regulators, binders, tackifiers, and also fertilisers or other active ingredients. Preferred preparations have especially the following compositions: (%=percent by weight)

| A1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| cyclohexanone | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| A2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| arom. hydrocarbon mixture $C_9$-$C_{12}$ | 75% | 60% | — | — |

The solutions are suitable for use in the form of microdrops.

| A3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| A4. Coated granules | a) | b) | c) |
|---|---|---|---|
| active ingredient mixture | 0.1% | 5% | 15% |
| highly dispersed silicic acid | 0.9% | 2% | 2% |
| inorganic carrier (0.1-1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

| A5. Coated granules | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier (AE 0.1-1 mm) e.g. $CaCO_3$ or $SiO_2$ | 98.0% | 92% | 80% |

The finely ground active ingredient is uniformly applied to the carrier moistened with polyethylene glycol. Non-dusty coated granules are obtained in this manner.

| A6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| A7. Dusts | a) | b) | c) |
|---|---|---|---|
| active ingredient mixture | 0.1% | 1% | 5% |
| talc | 39.9% | 49% | 35% |
| kaolin | 60.0% | 50% | 60% |

Ready-to-use dusts are obtained by mixing the active ingredient with the carriers and grinding the mixture in a suitable mill

| A8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

Example 34

Gel Formulation

The names of the formulation components are given according to the terminology of the registering authorities and their quantity is in grams per 100 g.

| Gel | /100 g |
|---|---|
| Active compound 2-chloro-6-(4-hydroxyanilino)purine (2Cl4OHAP) | 1.0 g |

| Gel | /100 g |
|---|---|
| butylhydroxytoluenum (Nipanox BHT) | 0.2 g |
| butylparaben (Nipabutyl) | 0.2 g |
| diethylene glycol monoethyl ether (Transcutol P) | 10.0 g |
| silica colloidalis anhydrica (Zeopharm 177) | 5.0 g |
| propylene glycol laurate (Lauroglycol FCC) | 83.6 g |

The gel consistence may be additionally modified by addition of silica colloidalis anhydrica. It is again expected that the transdermal Transcutol P/Lauroglycol FCC system will increase the efficiency of active compound. Silica colloidalis anhydrica will probably slow down the penetration of the active substance.

Example 35

Preparation Procedure of a Skin Application Form

Ointment

The names of the formulation components are given according to the terminology of registering authorities and their quantity is in grams per 200 g.

| | /200g |
|---|---|
| Active compound 2-chloro-6-(4-hydroxyanilino)purine (2Cl4OHAP) | 2.0 g |
| butylhydroxytoluenum (Nipanox BHT) 200018035611NP | 0.4 g |
| butylparaben (Nipabutyl) | 0.4 g |
| diethylene glycol monoethyl ether (Transcutol P) 3260/02 | 20.0 g |
| glycerol dibehenate (Compritol 888 ATO) 3123/04 | 44.0 g |
| Propylene glycol laurate (Lauroglycol FCC) 3219/00 | 133.2 g |

Recommended Procedure

Phase A 2 grams of the active ingredient were dissolved in 20 g of Transcutol P while stirring continuously at room temperature in a separate glass or stainless-steel container. The dissolution process may be accelerated by heating the solution to a maximal temperature of 40° C.

Phase B 0.4 grams of Nipanox BHT and 0.4 g of Nipabutyl were dissolved while stiffing continuously in 133.2 g of Laurogly- col FCC at a temperature of approximately 70° C. in another separate glass or stainless-steel container. The clear oily solution is heated to a temperature of approximately 80° C. and 44 g of Compritol 888 ATO are melted in it while stirring continuously. The clear oily solution is cooled down to approximately 60° C. and during continuous stirring and cooling down is mixed with phase A. The resulting whitish ointment-like substance is divided into approximately 15 gram portions and filled into prearranged plastic containers.

Example 36

Formulation of a Composition for Topical Application to the Skin

A composition for topical application to the skin contains the following ingredients by weight %:

| Active compound 2-chloro-6-(4-hydroxyanilino)purine (2Cl4OHAP) | 0.1% |
|---|---|
| Oil phase | |
| Cetyl alcohol | 5.0% |
| Glyceryl monostearate | 15.0% |
| Sorbitan monooleate | 0.3% |
| Polysorbate 80 USP | 0.3% |
| Aqueous phase | |
| Methylcellulose 100 cps | 1.0% |
| Methyl paraben | 0.25% |
| Propyl paraben | 0.15% |
| Purified water | q.s. to 100% |

Methylcellulose was dispersed in the hot water containing methyl paraben and propyl paraben. The mixture was then heated to 72° C. and added to the oil phase which was heated to 70° C. while stirring continuously. The active compound was added after cooling the mixture to the temperature of 35° C. and the resulting mixture was stirred continuously until cooling down.

This composition is applied to the skin on at least daily basis until the desired skin-ameliorating (anti-ageing) effect is reached.

The invention claimed is:

1. A method for inhibiting cytokinin oxidase/dehydrogenase, comprising:
   administering, to at least one of plant, mammal, microorganism, yeast and fungal cells, to delay senescence of said at least one of said plant, mammal, microorganism, yeast and fungal cells, an effective amount of at least one of a substituted 6-anilinopurine derivative of the general formula I

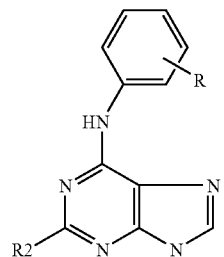

and the pharmaceutically acceptable salts thereof with alkali metals, ammonium or amines, in the form of racemates or optically active isomers, as well as their addition salts with acids, wherein;
R denotes one to five substituents independently selected from the group comprising hydrogen, halogen, hydroxyl, amino, alkyloxy and alkyl group, and
R2 denotes amino, halogen, nitro, thio, or alkylthio group.

2. The method according to claim 1 wherein the substituted 6-anilinopurine derivatives of the general formula I, are selected from the group consisting of 2-(chloro, fluoro, bromo, amino, nitro, thio, methylthio)-6-anilinopurine, 2-(chloro, fluoro, bromo, amino, nitro, thio, methylthio)-6-(2-chloroanilino)purine, 2-(chloro, fluoro, bromo, amino, nitro, thio, methylthio)-6-(3-chloroanilino)purine, 2-(chloro, fluoro, bromo, amino, nitro, thio, methylthio)-6-(4-chloroanilino)purine, 2-(chloro, fluoro, bromo, amino, nitro, thio, methylthio)-6-(2-fluoroanilino)purine, 2-(chloro, fluoro, bromo, amino, nitro, thio, methylthio)-6-(3-fluoroanilino) purine, 2-(chloro, fluoro, bromo, amino, nitro, thio, methylthio)-6-(4-fluoroanilino)purine, 2-(chloro, fluoro, bromo, amino, nitro, thio, methylthio)-6-(2-bromoanilino)purine, 2-(chloro, fluoro, bromo, amino, nitro, thio, methylthio)-6-(3-bromoanilino)purine, 2-(chloro, fluoro, bromo, amino, nitro, thio, methylthio)-6-(4-bromoanilino)purine, 2-(chloro, fluoro, bromo, amino, nitro, thio, methylthio)-6-(2-methoxyanilino)purine, 2-(chloro, fluoro, bromo, amino, nitro, thio, methylthio)-6-(3-methoxyanilino)purine, 2-(chloro, fluoro, bromo, amino, nitro, thio, methylthio)-6-(4-methoxyanilino)purine, 2-(chloro, fluoro, bromo, amino, nitro, thio, methylthio)-6-(2-ethoxyanilino)purine, 2-(chloro, fluoro, bromo, amino, nitro, thio, methylthio)-6-(3-ethoxyanilino)purine, 2-(chloro, fluoro, bromo, amino, nitro, thio, methylthio)-6-(4-ethoxyanilino)purine, 2-(chloro, fluoro, bromo, amino, nitro, thio, methylthio)-6-(2-aminoanilino) purine, 2-(chloro, fluoro, bromo, amino, nitro, thio, methylthio)-6-(3-aminoanilino)purine, 2-(chloro, fluoro, bromo, amino, nitro, thio, methylthio)-6-(4-aminoanilino)purine, 2-(chloro, fluoro, bromo, amino, nitro, thio, methylthio)-6-(2-methylanilino)purine, 2-(chloro, fluoro, bromo, amino, nitro, thio, methylthio)-6-(3-methylanilino)purine, 2-(chloro, fluoro, bromo, amino, nitro, thio, methylthio)-6-(4-methylanilino)purine, 2-(chloro, fluoro, bromo, amino, nitro, thio, methylthio)-6-(2-hydroxyanilino)purine, 2-(chloro, fluoro, bromo, amino, nitro, thio, methylthio)-6-(3-hydroxyanilino)purine, 2-(chloro, fluoro, bromo, amino, nitro, thio, methylthio)-6-(4-hydroxyanilino)purine, 2-(chloro, fluoro, bromo, amino, nitro, thio, methylthio)-6-(2,3-difluoroanilino)purine, 2-(chloro, fluoro, bromo, amino, nitro, thio, methylthio)-6-(2,4-difluoroanilino)purine, 2-(chloro, fluoro, bromo, amino, nitro, thio, methylthio)-6-(2,3,4-trifluoroanilino)purine,2-(chloro, fluoro, bromo, amino, nitro, thio, methylthio)-6- (2,4,5-trifluoroanilino)purine,2-(chloro, fluoro, bromo, amino, nitro, thio, methylthio)-6- (2,3-dichloroanilino)purine,2-(chloro, fluoro, bromo, amino, nitro, thio, methylthio)-6- (2,4-dichloroanilino)purine,2-(chloro, fluoro, bromo, amino, nitro, thio, methylthio)-6- (2,4-dimethoxyanilino)purine,2-(chloro, fluoro, bromo, amino, nitro, thio, methylthio)-6- (2,3-dimethoxyanilino)purine,2-(chloro, fluoro, bromo, amino, nitro, thio, methylthio)-6- (3,4-dimethoxyanilino)purine,2-(chloro, fluoro, bromo, amino, nitro, thio, methylthio)-6- (2,5-dimethoxyanilino)purine,2-(chloro, fluoro, bromo, amino, nitro, thio, methylthio)-6- (3,4,5-trimethoxyanilino)purine,2-(amino, chloro, fluoro, bromo, amino, nitro, thio, methylthio)-6-(2,4,6-trimethoxyanilino)purine,2-(chloro, fluoro, bromo, amino, nitro, thio, methylthio)-6- (2,3-dimethylanilino)purine,2-(chloro, fluoro, bromo, amino, nitro, thio, methylthio)-6- (2,4-dimethylanilino)purine,2-(chloro, fluoro, bromo, amino, nitro, thio, methylthio)-6- (3,4-dimethylanilino)purine,2-(chloro, fluoro, bromo, amino, nitro, thio, methylthio)-6- (3,5-dimethylanilino)purine,2-(chloro, fluoro, bromo, amino, nitro, thio, methylthio)-6- (2,3-dihydroxyanilino)purine,2-(chloro, fluoro, bromo, amino, nitro, thio, methylthio)-6- (2,4-dihydroxyanilino)purine,2-(chloro, fluoro, bromo, amino, nitro, thio, methylthio)-6- (2,5-dihydroxyanilino)purine,2-(amino, chloro, fluoro, bromo, amino, nitro, thio, methylthio)-6- (3,5-dihydroxyanilino)purine,2-(chloro, fluoro, bromo, amino, nitro, thio, methylthio)-6- (3-hydroxy-2-methylanilino)purine,2-(chloro, fluoro, bromo, amino, nitro, thio, methylthio)-6- (3-hydroxy-4-methylanilino)purine,2-(chloro, fluoro, bromo, amino, nitro, thio, methylthio)-6- (2-hydroxy-5-methylanilino)purine,2-(chloro, fluoro, bromo, amino, nitro, thio, methylthio)-6- (3-hydroxy-2-methoxylanilino)purine, 2-(chloro, fluoro, bromo, amino, nitro, thio, methylthio)-6- (3-hydroxy-4-methoxylanilino)purine,2-(chloro, fluoro, bromo, amino, nitro, thio, methylthio)-6- (2-hydroxy-3-methoxylanilino)purine,2-(chloro, fluoro, bromo, amino, nitro, thio, methylthio)-6- (2-hydroxy-5-methoxylanilino) purine,2-(chloro, fluoro, bromo, amino, nitro, thio, methylthio)-6- (4-hydroxy-3,5-dimethoxylanilino)purine,2-(amino, chloro, fluoro, hydroxy, thio, methylthio)-6- (2-chloro-4-methoxyanilino)purine,2-(amino, chloro, fluoro, bromo, nitro, thio, methylthio)-6- (2-chloro-5-methoxyanilino)purine, 2-(amino, chloro, fluoro, bromo, amino, nitro, thio, methylthio)-6- (2-chloro-3-methoxyanilino)purine,2-(chloro, fluoro, bromo, amino, nitro, thio, methylthio)-6- (2-bromo-3-methoxyanilino)purine,2-(chloro, fluoro, bromo, amino, nitro, thio, methylthio)-6- (2-methoxy-3-chloroanilino)purine,2-(chloro, fluoro, bromo, amino, nitro, thio, methylthio)-6- (2-methoxy-4-chloroanilino)purine, and the pharmaceutically acceptable salts thereof with alkali metals, ammonium or amines, in the forms of racemates or optically active isomers, as well as their addition salts with acids.

3. The method according to claim 1 wherein the substituted 6-anilinopurine derivatives of the general formula I, are selected from the group consisting of 2-(chloro, fluoro, bromo, amino, nitro, methylthio)-6- (3-methoxyanilino)purine, 2-(chloro, fluoro, bromo, amino, nitro, methylthio)-6- (2-hydroxy-3-methoxyanilino)purine, 2-(chloro, fluoro, bromo, amino, nitro, methylthio)-6- (2-chloro-3-methoxyanilino)purine, 2-(chloro, fluoro, bromo, amino, nitro, methylthio)-6- (2-bromo-3-methoxyanilino)purine, 2-(chloro, fluoro, bromo, amino, nitro, methylthio)-6- (4-hydroxyanilino)purine, and the pharmaceutically acceptable salts thereof with alkali metals, ammonium or amines, in the forms of racemates or optically active isomers, as well as their addition salts with acids.

4. The method according to claim 1 including administering the substituted 6-anilinopurine derivatives of the general formula I to at least one of fibroblasts and keratinocytes for delaying senescence of said at least one of fibroblasts and keratinocytes.

5. The method according to claim 1 including administering the substituted 6-anilinopurine derivatives of the general formula I to tissue cultures for stimulating proliferation and morphogenesis of said tissue cultures.

6. The method according to claim 1 including administering the substituted 6-anilinopurine derivatives of the general formula I to agricultural products for increasing of yield and quality of said agricultural products.

7. The method according to claim 1 including administering the substituted 6-anilinopurine derivatives of the general formula I to a mammal for suppression of immunostimulation or for suppression of transplant rejection in said mammal.

8. Cosmetic and growth-regulatory preparations comprising at least one substituted 6-anilinopurine derivatives of the general formula I or the salts thereof with alkali metals, ammonium or amines, in the forms of racemates or optically active isomers, or their addition salts with acids, and adjuvants wherein formula I comprises:

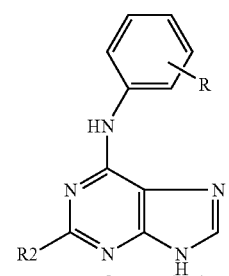

I and R denotes one to five substituents independently selected from the group comprising hydrogen, halogen, hydroxyl, amino, alkyloxy and alkyl group, and R2 denotes a nitro, thio, or alkylthio group.

9. The method according to claim 1 including administering the substituted 6-anilinopurine derivatives of the general formula I to mammal skin cells for delaying senescence of said mammalian skin cells.

* * * * *